(12) United States Patent
Hurson

(10) Patent No.: US 9,452,031 B2
(45) Date of Patent: Sep. 27, 2016

(54) DENTAL IMPLANT AND DENTAL COMPONENT CONNECTION

(71) Applicant: Nobel Biocare Services AG, Zurich-Flughafen (CH)

(72) Inventor: Steven Hurson, Yorba Linda, CA (US)

(73) Assignee: Nobel Biocare Services AG (CH)

( * ) Notice: Subject to any disclaimer, the term of this patent is extended or adjusted under 35 U.S.C. 154(b) by 109 days.

(21) Appl. No.: 14/295,164

(22) Filed: Jun. 3, 2014

(65) Prior Publication Data

US 2014/0370459 A1 Dec. 18, 2014

Related U.S. Application Data

(63) Continuation of application No. 13/250,001, filed on Sep. 30, 2011, now abandoned, which is a continuation of application No. 11/739,024, filed on Apr. 23, 2007, now Pat. No. 8,038,442.

(51) Int. Cl.
*A61C 8/00* (2006.01)
*A61C 13/271* (2006.01)

(52) U.S. Cl.
CPC .............. *A61C 8/006* (2013.01); *A61C 8/005* (2013.01); *A61C 8/0022* (2013.01); *A61C 8/0068* (2013.01); *A61C 8/0069* (2013.01); *A61C 13/26* (2013.01)

(58) Field of Classification Search
CPC .. A61C 8/006; A61C 8/0068; A61C 8/0069; A61C 13/26; A61C 8/027; A61C 5/08; A61C 8/0062; A61C 8/001
USPC .................................................. 433/172–176
See application file for complete search history.

(56) References Cited

U.S. PATENT DOCUMENTS

| 1,698,951 A | 1/1929 | Holmes |
| 2,215,770 A | 9/1940 | Sheffield |

(Continued)

FOREIGN PATENT DOCUMENTS

| CN | 1251509 | 4/2000 |
| CN | 1668255 | 9/2005 |

(Continued)

OTHER PUBLICATIONS

Mar. 11, 2004 International Search Report, Application No. PCT/SE2003/001973, 3 pages (of-record in the parent application).

(Continued)

*Primary Examiner* — Nicholas Lucchesi
(74) *Attorney, Agent, or Firm* — Knobbe Martens Olson & Bear, LLP

(57) ABSTRACT

A dental implant, components, and kit are provided. The implant can include a body, an attachment structure for attaching the implant to bone, and a recess. The recess can be disposed within the body and open towards a proximal end thereof. The recess can include a proximally-disposed receiving chamber and a distally-disposed threaded chamber. The receiving chamber can include an interlock chamber, which can be disposed at a distal end of the receiving chamber and have a polygonal cross-section. The implant can be multi-functional such that components for various dental prostheses and procedures can be provided having portions that can, for example, engage the interlock chamber of the implant, mate with the receiving chamber of the implant, and/or mate with the proximal end the implant for supporting the prosthesis and/or facilitating the procedure.

12 Claims, 25 Drawing Sheets

(56) References Cited

U.S. PATENT DOCUMENTS

| | | | |
|---|---|---|---|
| 3,672,058 A | 6/1972 | Nikoghossian | |
| 3,797,113 A | 3/1974 | Brainin | |
| 3,849,887 A | 11/1974 | Brainin | |
| 4,103,422 A | 8/1978 | Weiss et al. | |
| 4,406,623 A | 9/1983 | Grafelmann et al. | |
| 4,431,416 A | 2/1984 | Niznick | |
| 4,468,200 A | 8/1984 | Munch | |
| 4,547,157 A | 10/1985 | Driskell | |
| 4,645,453 A | 2/1987 | Niznick | |
| 4,713,003 A | 12/1987 | Symington et al. | |
| 4,738,623 A | 4/1988 | Driskell | |
| 4,758,161 A | 7/1988 | Niznick | |
| 4,826,434 A | 5/1989 | Krueger | |
| 4,863,383 A | 9/1989 | Grafelmann | |
| 4,932,868 A | 6/1990 | Linkow et al. | |
| 4,960,381 A | 10/1990 | Niznick | |
| 4,976,739 A | 12/1990 | Duthie, Jr. | |
| 5,000,686 A | 3/1991 | Lazzara et al. | |
| 5,007,835 A | 4/1991 | Valen | |
| 5,061,181 A | 10/1991 | Niznick | |
| 5,062,800 A | 11/1991 | Niznick | |
| 5,071,350 A | 12/1991 | Niznick | |
| 5,074,790 A | 12/1991 | Bauer | |
| 5,076,788 A | 12/1991 | Niznick | |
| RE33,796 E | 1/1992 | Niznick | |
| 5,078,607 A | 1/1992 | Niznick | |
| 5,087,201 A | 2/1992 | Mondani et al. | |
| 5,195,892 A | 3/1993 | Gersberg | |
| 5,226,766 A | 7/1993 | Lasner | |
| 5,230,590 A | 7/1993 | Bohannan et al. | |
| 5,328,371 A | 7/1994 | Hund et al. | |
| 5,343,391 A | 8/1994 | Mushabac | |
| 5,350,302 A * | 9/1994 | Marlin | A61C 8/0048 433/173 |
| 5,427,527 A | 6/1995 | Niznick et al. | |
| 5,433,606 A | 7/1995 | Niznick | |
| 5,435,723 A | 7/1995 | O'Brien | |
| 5,439,381 A | 8/1995 | Cohen | |
| 5,484,286 A | 1/1996 | Hansson | |
| 5,527,183 A | 6/1996 | O'Brien | |
| 5,571,017 A | 11/1996 | Niznick | |
| 5,580,246 A | 12/1996 | Fried et al. | |
| 5,584,629 A | 12/1996 | Bailey et al. | |
| 5,601,429 A | 2/1997 | Blacklock | |
| 5,628,630 A | 5/1997 | Misch et al. | |
| 5,639,237 A | 6/1997 | Fontenot | |
| 5,642,996 A | 7/1997 | Mochida et al. | |
| 5,674,072 A | 10/1997 | Moser et al. | |
| 5,725,375 A | 3/1998 | Rogers | |
| 5,733,123 A | 3/1998 | Blacklock et al. | |
| 5,782,918 A | 7/1998 | Klardie et al. | |
| 5,795,160 A | 8/1998 | Hahn et al. | |
| 5,810,590 A | 9/1998 | Fried et al. | |
| 5,816,812 A | 10/1998 | Kownacki et al. | |
| 5,823,776 A | 10/1998 | Duerr et al. | |
| 5,823,777 A | 10/1998 | Misch et al. | |
| 5,871,356 A | 2/1999 | Guedj | |
| 5,876,453 A | 3/1999 | Beaty | |
| 5,897,319 A | 4/1999 | Wagner et al. | |
| 5,915,968 A | 6/1999 | Kirsch et al. | |
| 5,938,444 A | 8/1999 | Hansson et al. | |
| 5,967,783 A | 10/1999 | Ura | |
| 6,095,817 A | 8/2000 | Wagner et al. | |
| 6,116,904 A | 9/2000 | Kirsch et al. | |
| 6,129,730 A | 10/2000 | Bono et al. | |
| 6,135,772 A | 10/2000 | Jones | |
| 6,149,432 A | 11/2000 | Shaw et al. | |
| 6,200,345 B1 | 3/2001 | Morgan | |
| 6,227,859 B1 | 5/2001 | Sutter | |
| 6,273,722 B1 | 8/2001 | Phillips | |
| 6,287,117 B1 | 9/2001 | Niznick | |
| 6,312,259 B1 | 11/2001 | Kvarnstrom et al. | |
| 6,315,564 B1 | 11/2001 | Levisman | |
| 6,358,050 B1 | 3/2002 | Bergstrom et al. | |
| 6,394,806 B1 | 5/2002 | Kumar | |
| 6,402,515 B1 | 6/2002 | Palti | |
| 6,419,491 B1 | 7/2002 | Ricci et al. | |
| 6,481,760 B1 | 11/2002 | Noel et al. | |
| 6,626,671 B2 | 9/2003 | Klardie et al. | |
| 6,655,962 B1 | 12/2003 | Kennard | |
| 6,679,701 B1 | 1/2004 | Blacklock | |
| 6,726,689 B2 | 4/2004 | Jackson | |
| 6,733,291 B1 | 5/2004 | Hurson | |
| 6,733,503 B2 | 5/2004 | Layrolle et al. | |
| 6,769,913 B2 | 8/2004 | Hurson | |
| 6,913,465 B2 | 7/2005 | Howlett et al. | |
| 6,955,258 B2 | 10/2005 | Howlett et al. | |
| 7,014,464 B2 | 3/2006 | Niznick | |
| 7,108,510 B2 | 9/2006 | Niznick | |
| 7,249,949 B2 | 7/2007 | Carter | |
| 7,273,373 B2 | 9/2007 | Horiuchi | |
| 7,281,925 B2 | 10/2007 | Hall | |
| 7,383,163 B2 | 6/2008 | Holberg | |
| 2002/0102518 A1 | 8/2002 | Mena | |
| 2002/0106612 A1 | 8/2002 | Back et al. | |
| 2002/0177106 A1 | 11/2002 | May et al. | |
| 2004/0121289 A1 | 6/2004 | Miller | |
| 2005/0147942 A1 | 7/2005 | Hall | |
| 2005/0186537 A1 | 8/2005 | Gersberg | |
| 2005/0214714 A1 | 9/2005 | Wohrle | |
| 2005/0260540 A1 | 11/2005 | Hall | |
| 2005/0287497 A1 | 12/2005 | Carter | |
| 2006/0084035 A1 | 4/2006 | Volz | |
| 2006/0172257 A1 | 8/2006 | Niznick | |
| 2006/0172258 A1 | 8/2006 | Niznick | |
| 2006/0183078 A1 | 8/2006 | Niznick | |
| 2006/0246397 A1 | 11/2006 | Wolf | |
| 2007/0037121 A1 | 2/2007 | Carter | |
| 2007/0099153 A1 | 5/2007 | Fromovich | |
| 2007/0202463 A1 | 8/2007 | Sanchez et al. | |
| 2007/0298379 A1 | 12/2007 | D'Alise | |
| 2008/0014556 A1 | 1/2008 | Neumeyer | |
| 2008/0032263 A1 | 2/2008 | Bondar | |
| 2008/0032264 A1 | 2/2008 | Hall | |
| 2008/0081316 A1 | 4/2008 | Chung | |
| 2008/0261175 A1 | 10/2008 | Hurson | |
| 2009/0305192 A1 | 12/2009 | Hall | |
| 2012/0021381 A1 | 1/2012 | Hurson | |

FOREIGN PATENT DOCUMENTS

| | | | |
|---|---|---|---|
| DE | 10231743 | | 2/2004 |
| EP | 0377068 | A1 | 11/1990 |
| EP | 0475358 | | 3/1992 |
| EP | 0 707 835 | | 4/1996 |
| EP | 1396236 | | 3/2004 |
| EP | 1624826 | A1 | 2/2006 |
| EP | 1728486 | | 6/2006 |
| EP | 1624826 | A4 | 5/2007 |
| FR | 2 600 246 | | 12/1987 |
| JP | 8-501962 | | 3/1996 |
| JP | 3026125 | | 4/1996 |
| JP | 10-052445 | | 2/1998 |
| RU | 2190373 | | 10/2002 |
| RU | 2202982 | | 4/2003 |
| RU | 2202984 | | 4/2003 |
| RU | 2204356 | | 5/2003 |
| RU | 2262324 | | 10/2005 |
| RU | 2273464 | | 4/2006 |
| WO | WO 94/07428 | | 4/1994 |
| WO | WO 94/09717 | | 5/1994 |
| WO | WO 95/09583 | | 4/1995 |
| WO | WO 97/05238 | | 2/1997 |
| WO | WO 99/23971 | | 5/1999 |
| WO | WO 00/00103 | | 1/2000 |
| WO | WO 00/72775 | | 12/2000 |
| WO | WO 00/72777 | | 12/2000 |
| WO | WO 01/74412 | | 10/2001 |
| WO | WO 01/76653 | | 10/2001 |
| WO | WO 03/015654 | A1 | 2/2003 |
| WO | WO 03/030767 | | 4/2003 |
| WO | WO 03/034951 | | 5/2003 |
| WO | WO 03/055405 | | 7/2003 |
| WO | WO 03/055406 | A1 | 7/2003 |

(56) References Cited

FOREIGN PATENT DOCUMENTS

| WO | WO 03/063085 | 7/2003 |
|---|---|---|
| WO | WO 2004/058091 | 7/2004 |
| WO | WO 2004/103202 | 12/2004 |
| WO | WO 2005/044132 | 5/2005 |
| WO | WO 2005/044135 | 5/2005 |
| WO | WO 2005/117742 | 12/2005 |
| WO | WO 2006/012273 | 2/2006 |
| WO | WO 2007/086622 A1 | 8/2007 |
| WO | WO 2008/096294 A1 | 8/2008 |

OTHER PUBLICATIONS 3.8D series Threaded Implant, dental implant sold before Sep. 27, 1999, Nobel Biocare (of-record in the parent application).

English translation of WO 05/117742 to Neumeyer, Dec. 15, 2005 (of-record in the parent application).

Fernandes, Americo, DMD, "Combining the Single Implant With a CAD/CAM Restoration", Dentistry Today, vol. 20 No. 12, dated Dec. 2001, (Note Figure 9) (of-record in the parent application).

International Preliminary Report on Patentability for PCT Application No. PCT/IL2004/000438 filed May 23, 2004. Publication No. WO 04/103202 A1 published Dec. 2, 2004 (of-record in the parent application).

International Search Report for Application No. EP04734484 filed May 23, 2004. Publication No. EP 1624826 A1, published Feb. 15, 2006 (of-record in the parent application).

Niznick, Gerald A., DMD, MSD. "Proactive Nobel Active New Presentation" Implant Direct™, Oct. 16, 2007 (of-record in the parent application).

Supplementary European Search Report for Application No. EP04734484 filed May 23, 2004. Publication No. EP 1624826 A4, published May 30, 2007 (of-record in the parent application).

International Search Report for Application No. PCT/SE2003/001973, mailed Mar. 11, 2004 in 3 pages.

\* cited by examiner

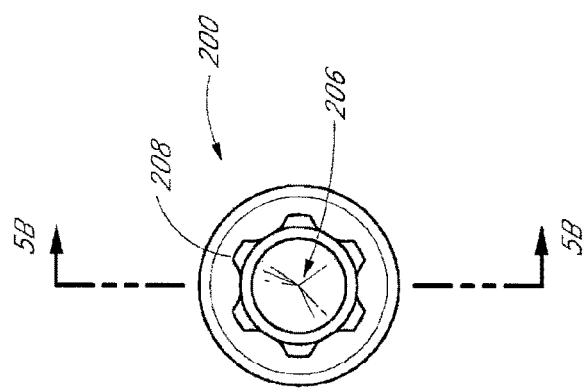
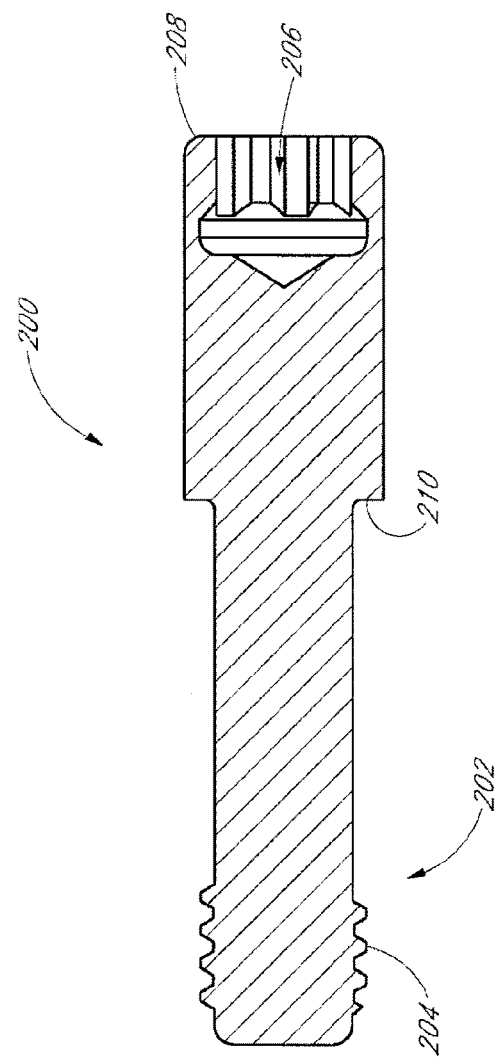
FIG. 5A
FIG. 5B

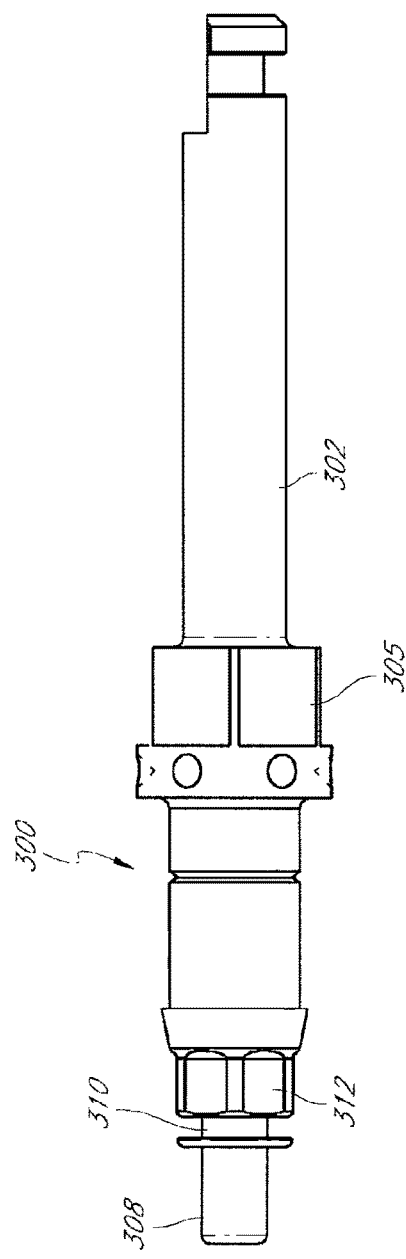
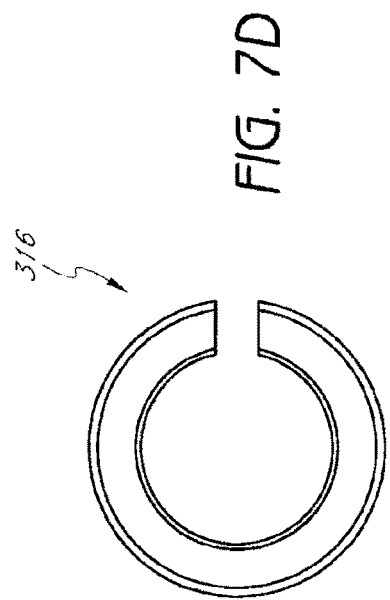
FIG. 7C
FIG. 7D

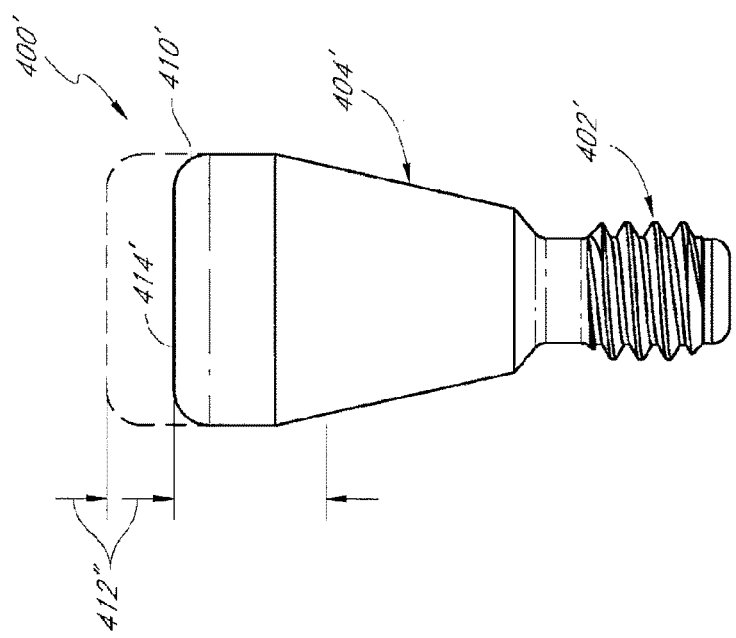
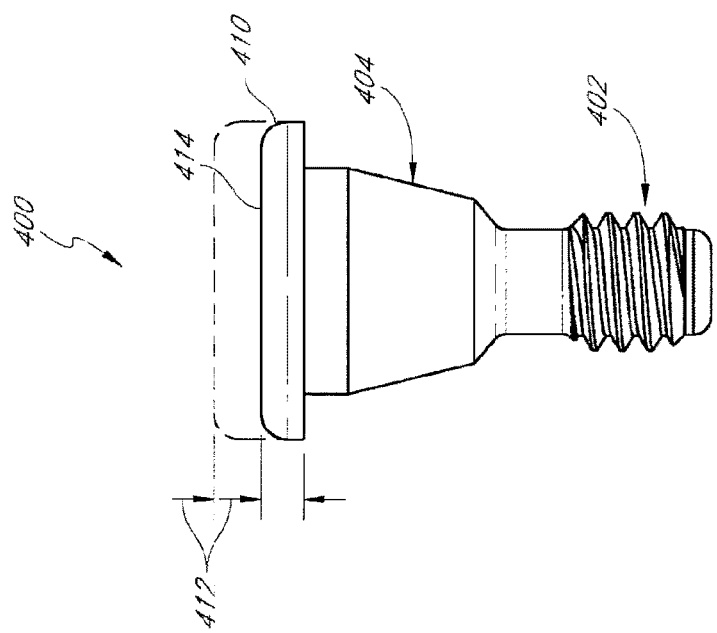

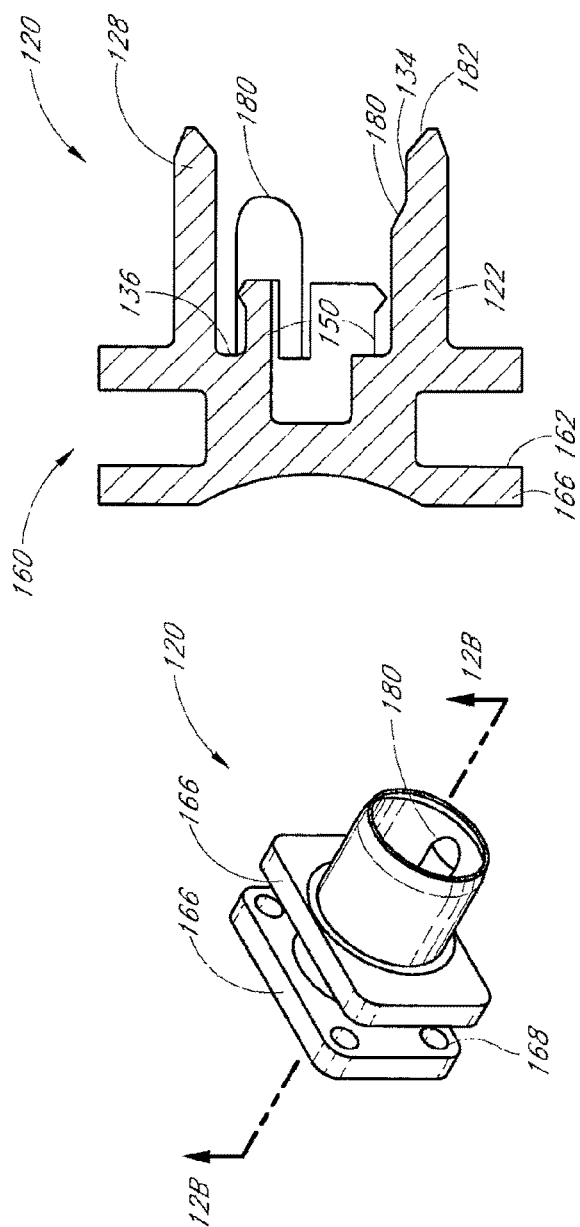

FIG. 17A
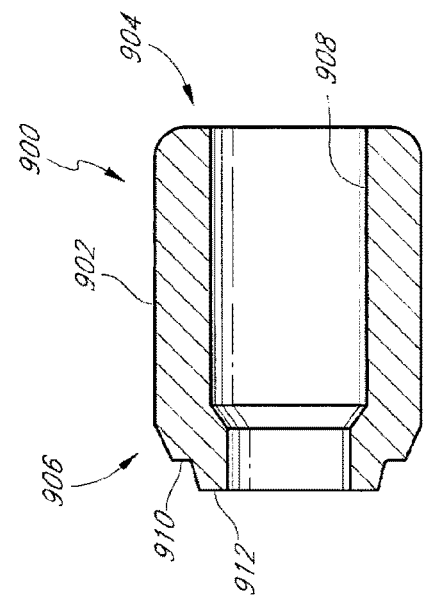
FIG. 17C
FIG. 17B

DENTAL IMPLANT AND DENTAL COMPONENT CONNECTION

RELATED APPLICATION INFORMATION

The present application is a continuation of U.S. patent application Ser. No. 13/250,001, filed Sep. 30, 2011, which is a continuation of U.S. patent application Ser. No. 11/739,024, filed Apr. 23, 2007, now U.S. Pat. No. 8,038,442, the disclosure of both of which is incorporated by reference herein in its entirety.

BACKGROUND

1. Field of the Inventions

The present inventions relate generally to implant dentistry and, more specifically, to dental implants and their mating components.

2. Description of the Related Art

Implant dentistry involves the restoration of one or more teeth in a patient's mouth using artificial components. Such artificial components typically include a dental implant that supports a prosthetic tooth (e.g., a crown), an implant-supported bridge or an implant-supported denture. The dental implant is typically fabricated from pure titanium or a titanium alloy. The dental implant can include a body portion and a collar. The body portion is configured to extend into and osseointegrate with the alveolar bone. The top surface of the collar typically lies flush with the crest of the jawbone. An abutment (e.g., a final abutment) typically lies on the top surface and extends through the soft tissue, which lies above the alveolar bone. Recently, some dental implants have collars that extend above the crest of the jawbone and through the soft tissue. In certain indications, a dental implant can be used to replace a single tooth. In such indications, the dental implant is configured to support a single dental restoration (e.g., a crown), which can be mounted directly onto the implant or onto an abutment. In other indications, one or more dental implants are used to replace a plurality of teeth. In such indications, the one or more implants can be configured to support an implant supported bridge or an implant supported denture that can be attached directly to the implant or indirectly through a multi-unit abutment.

Various connection platforms are known in the art for providing a connection interface between a dental implant and an abutment or other mating component. In general, the connection platforms can be characterized as external or internal. An example of an external connection platform is a dental implant with a hexagonal protrusion at the proximal end of the implant. See e.g., the Brånemark System® sold by Nobel Biocare™. An example of an internal connection platform can be found in U.S. Pat. No. 6,733,291, which describes a dental implant with an internal multi-lobed interlock for mating with an abutment. See also NobelReplace™ sold by Nobel Biocare™. Another example of an internal connection is U.S. Pat. No. 4,960,381, which discloses a dental implant comprising a socket with a conical upper portion, a registration portion below the conical upper portion and an internally-threaded shaft below the registration portion.

While such prior art dental implants have been successful, there is a continuing desire to improve the connection platform between the dental implant and the abutment. Such an improved platform would advantageously provide a robust anti-rotational structure to resist rotation and provide an indexing function between a mating component and the dental implant while also providing an enhanced seal between the mating component and the implant. It would also be desirable for the connection platform to accommodate various types of clinical indications such that the implant can be used to support both single dental restorations as well as implant supported bridges or dentures. In addition, it would be advantageous to continue to improve the dental implant's ability to osseointegrate with the alveolar bone and to generally promote gingival health and beauty.

SUMMARY OF THE INVENTION

Accordingly, one embodiment of the present inventions comprises a dental implant. The dental implant can comprise a body having an open socket formed in the body. The body can comprise a proximal end, a distal end, and an outer surface extending between the proximal end and the distal end. The body can have a longitudinal axis and the distal end can define a top surface that is substantially flat and perpendicular to the longitudinal axis of the implant. The open socket can be formed in the top surface of the body. The open socket can comprise at least one tapered surface extending from the top surface. In some embodiments, the top surface of the implant can have an outer periphery and an inner periphery defined by the open socket and wherein the distance between the outer periphery and the inner periphery is equal to or greater than at least 0.2 millimeters. In certain arrangements, the top surface of the implant can be used to support multi-unit dental restorations such as implant supported bridges and/or dentures.

In some embodiments, an interlock portion is formed below the tapered surface and the interlock portion includes at least one flat side that can form at least one of a square recess, a hexagonal recess, and an octagonal recess. In other embodiments, a portion of the at least one flat side can extend into the substantially conical portion of the open socket.

The dental implant can also be configured such that the at least one tapered surface forms a substantially conical portion that defines a conical half angle between about 10 degrees and about 20 degrees. In other embodiments, the substantially conical portion defines a conical half angle that is about 12 degrees. The ratio of the length of the conical portion and the length of the interlock portion can be between about 1:1. In one embodiment, the conical portion has a length measured vertically from the top surface of the implant of about 1 millimeter. In addition to and/or in the alternative, the interlock portion can have a length of about 1 millimeter.

In yet other embodiments, the dental implant can further comprise a substantially cylindrical portion positioned between the interlock portion and a threaded portion of the open socket. In yet other embodiments, the outer surface of the implant can be provided with a surface treated to enhance tissue growth.

In accordance with another embodiment of the present inventions, a dental implant is provided that comprises a body and an open socket formed in the body. The body can comprise a proximal end, a distal end, and an outer surface extending between the proximal end and the distal end. The body can have a longitudinal axis and the distal end can define a top surface. Further, the open socket can be formed in the top surface of the body. The open socket can comprise a substantially conical portion extending from the top surface, an interlock portion comprising at least one flat side positioned below the substantially conical portion, and a threaded portion comprising a thread positioned below the interlock region. In some embodiments, the ratio of the length of the conical portion and the length of the interlock portion is about 1:1.

In other embodiments, the at least one flat side of the interlock portion can form at least one of a square recess, a hexagonal recess, and an octagonal recess. A portion of the at least one flat side can extend into the substantially conical portion of the open socket. The substantially conical portion can define a conical half angle between about 10 degrees and about 20 degrees. Further, a portion of the at least one flat side can extend into at least ½ of the length of the substantially conical section.

In yet another embodiment of the present inventions, a system is provided that comprises a first dental component, a second dental component, and/or a third dental component. The first dental component can comprise a body comprising a proximal end, a distal end, and an outer surface extending between the proximal end and the distal end. The body can have a longitudinal axis and the distal end can define a top surface. The first dental component can also comprise an open socket formed in the top surface of the body. The open socket can comprise a substantially conical portion extending from the top surface, an interlock portion comprising at least one flat side positioned below the substantially conical portion, and a threaded portion comprising a thread positioned below the interlock region.

The system can include a second dental component that is configured to fit within the conical portion of the open socket of the implant and to engage the conical portion of the implant in a slip fit. In addition, the at least one flat side of the interlock portion can form at least one of a square recess, a hexagonal recess, and an octagonal recess. Further, the substantially conical portion can define a conical half angle between about 10 degrees and about 20 degrees.

A third dental component can comprise an upper portion and a lower portion configured to fit within the open socket of the implant. The lower portion can comprise an interlock region configured to mate with the interlock portion of the dental implant and a conical region configured to mate with conical portion of the dental implant in a tapered fit.

In another embodiment, the third dental component can comprise an upper surface and a lower portion to fit within the open socket. The lower portion can comprise a conical region configured to mate with the conical portion of the dental implant in a tapered fit and to extend into the interlock portion of the implant but not to engage the interlock portion. In such an embodiment, it is contemplated that the at least one flat side of the interlock portion can form at least one of a square recess, a hexagonal recess, and an octagonal recess. Further, the substantially conical portion can define a conical half angle between about 10 degrees and about 20 degrees.

BRIEF DESCRIPTION OF THE DRAWINGS

The abovementioned and other features of the inventions disclosed herein are described below with reference to the drawings of the preferred embodiments. The drawings contain the following figures:

FIG. 5A is a top view of a coupling element.

FIG. 5B is a cross-sectional side view taken through line 5B-5B of FIG. 5A.

FIG. 7C is a side view of another embodiment of an insertion tool.

FIG. 7D is a front view of a clip configured to be coupled to the insertion tool of FIG. 7c.

FIG. 8A is a side view of an abutment according to yet another embodiment.

FIG. 8B is a side view of another embodiment of an abutment.

FIG. 12A is a bottom perspective view of an embodiment of an impression coping that can be fitted onto the abutment illustrated in FIG. 9.

FIG. 12B is a cross-sectional side view of the impression coping of FIG. 12A.

FIG. 17A is a side perspective view of another embodiment of an abutment.

FIG. 17B is a side view of the abutment of FIG. 17A.

FIG. 17C is a cross-sectional side view of the abutment of FIG. 17A.

DETAILED DESCRIPTION OF THE PREFERRED EMBODIMENTS

FIGS. 1A-1D illustrate an embodiment of a dental implant 20 having certain features and aspects according the present inventions. As will be described in further detail below, the dental implant 20 can be used to support a single dental restoration (e.g., a crown) and/or can be used to support a plurality of dental restorations (e.g. an implant supported bridge or denture).

Figure 1A:
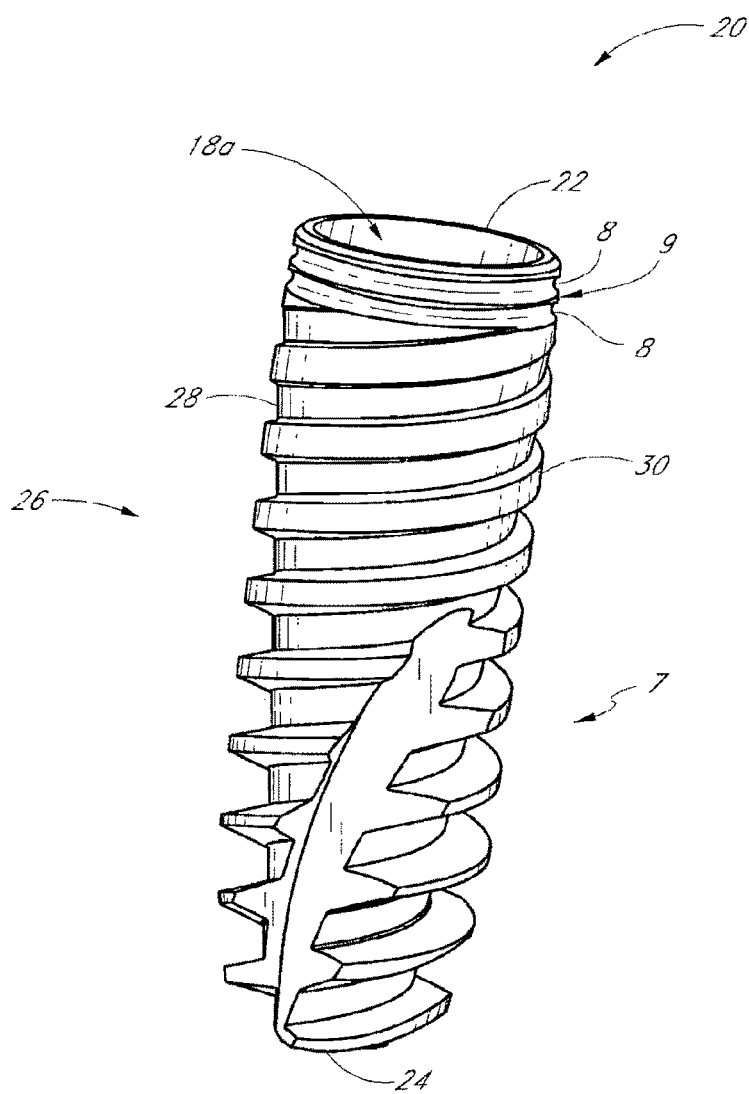
FIG. 1A is a top front perspective view of a dental implant in accordance with an embodiment of the present invention.

With initial reference to FIGS. 1A-1D, the illustrated implant 20 includes a connection portion 18a that can be used to connect the dental implant 20 to another dental component, such as a dental abutment, healing cap, impression coping, and/or implant supported bridge or denture, as will be described below. As best seen in FIG. 1A, the dental implant 20 can also include a body 26 that extends from a proximal end 22 of the implant 20 to a distal end 24 of the implant 20. The dental implant 20 can be made of titanium, although other materials can be used, such as various types of ceramics The body 26 preferably comprises an outer surface 28. In the illustrated arrangement, the outer surface 28 includes threads 30 that extend helically around the body 26. As is known in the art, the threads 30 can improve the dental implant's ability to osseointegrate with the alveolar bone and improve stability. However, in other embodiments, the body 26 can be unthreaded. In addition, the dental implant 20 can utilize various types of thread configurations. Examples of such thread configurations include the threaded implants sold under the trademarks NobelReplace™ Tapered and NobelReplace™ Straight, the threaded configurations described in PCT Application No. PCT/IL2004/00438, the entirety of which is incorporated herein by reference, and in Applicant's co-pending application filed on the same date as this application, entitled "DENTAL IMPLANT," the entirety of which is also incorporated herein by reference.

Figure 1B:
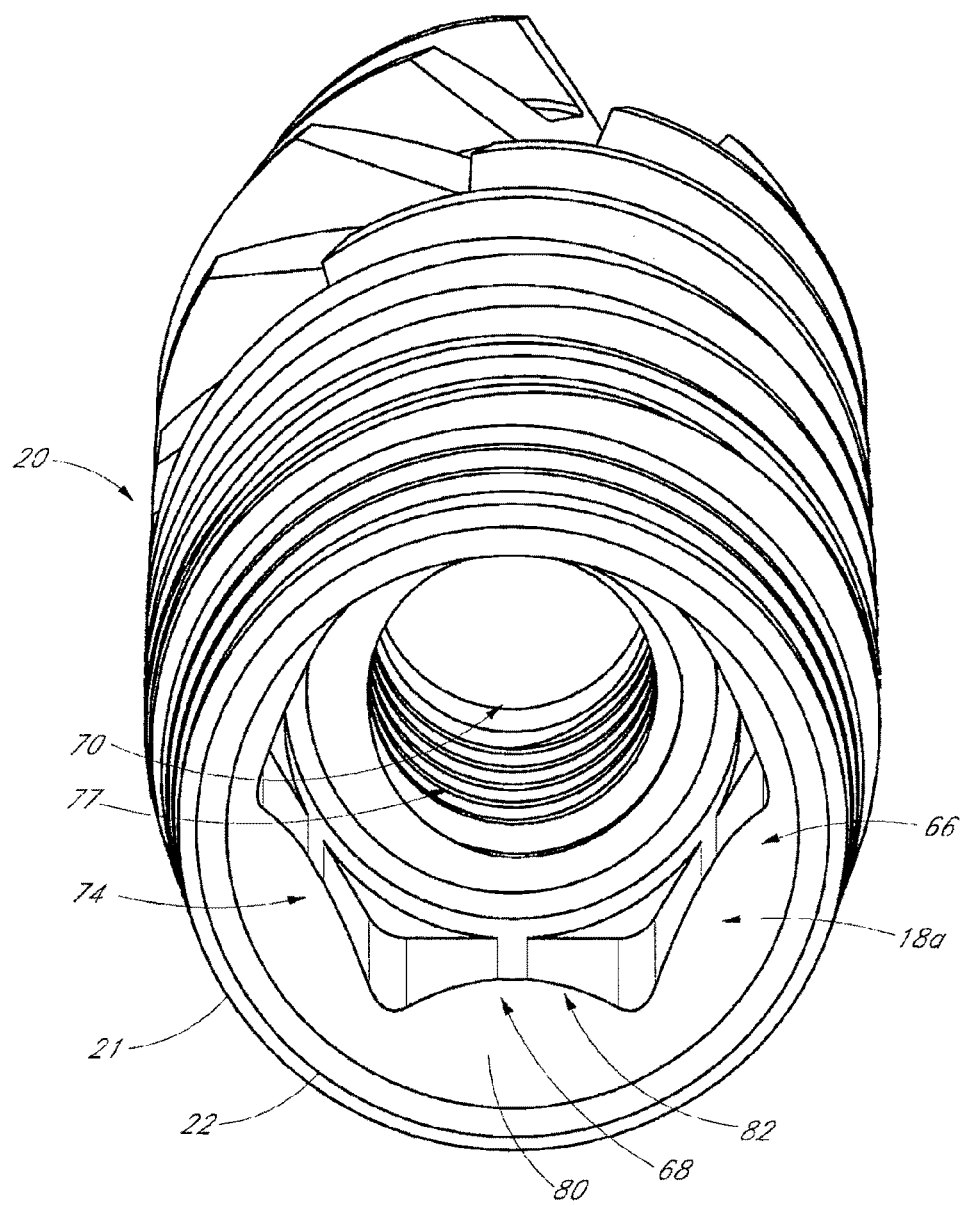
FIG. 1B is an enlarged top side perspective view of the dental implant of FIG. 1A.
Figure 1C:
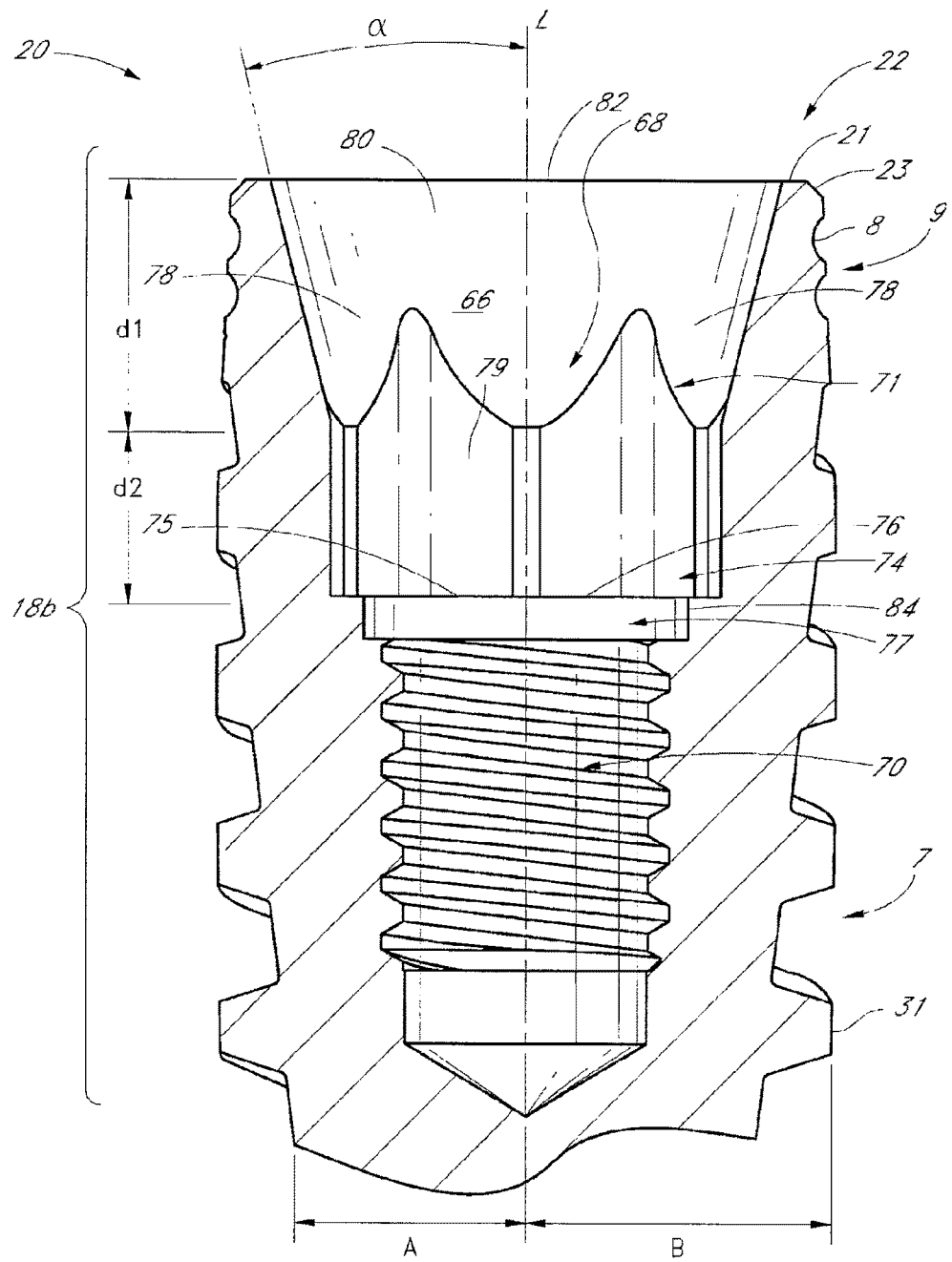
FIG. 1C is an enlarged cross-sectional side view of the dental implant of FIG. 1A.

With reference to FIGS. 1A and 1C, the body 26 can include a generally cylindrical proximal portion or collar 9 with a generally tapered distal portion 7. In the illustrated embodiment, the collar 9 can include a pair of circumferential generally semi-circular grooves 8, which in one embodiment have a width of about 150 microns across and a depth of about 50 microns. In modified embodiments, the collar 9 can be provided with more, less or no grooves and/or grooves with different dimensions and configurations. In other embodiments, the circumferential protrusions or micro-threads can be provided on the collar 9. In general, such structures on the collar 9 are advantageously configured to load the harder cortical bone through which the implant 20 is inserted but to a lesser extent as compared to the threads 30 of the implant 20, which can be configured to engage the spongy cancellous bone positioned below the cortical bone. In other embodiments, the collar 9 can be inwardly tapered or have a reverse taper.

With continued reference to FIG. 1A and FIG. 1C, as mention above, the threads 30 in the illustrated embodiment are relatively coarse threads configured to engage the spongy cancellous bone positioned below the cortical bone. In addition to aid retention forces in the cancellous bone, the body 26 preferably tapers at an angle A from the collar 9 to the distal end of the implant 20. In one embodiment, the angle A can vary along the length of the implant and in one embodiment the variable angle can vary such that the angle at the distal portion is shallower than that at the proximal portion. Further, the faces 31 of the threads 30 can also form a conical shape having an angle B that can also vary along the length of the implant 30. The angle defined by the faces 31 of the threads 30 can be different from the varying conical angle formed by the implant body 26. That is, the conical angle defined by the lower portion 34 of the implant body 26 can be shallower than the conical angle formed by the threads 30. Although the illustrated embodiment utilizes the aforementioned conical angle relations, other suitable relations may be used. Such suitable relations may comprise threads 30 that are not conical and define a generally cylindrical shape or threads 30 that define a conical angle that closely matches the conical angle the implant body 26. In other embodiments, the body 26 and/or the thread 30 faces 31 can be substantially cylindrical. It should also be appreciated that the body 26 can be configured to be self-tapping.

In addition to or as an alternative to the threads 30, the outer surface 28 of the implant 20 can be provided with various other surface features configured to promote osseointegration and/or soft tissue health. For example, the surface area of the outer surface 28 can be increased by roughening the implant body 26 in several different manners, such as, for example, by acid-etching, grit blasting, and/or machining. The outer surface 28 can also be coated with a substance configured to promote osseointegration (e.g. growth factor, Bone morphogenetic protein (BMP))). In some embodiments, the coating can result in decreasing or increasing the surface area of the implant body 26. Calcium phosphate ceramics, such as tricalcium phosphate (TCP) and hydroxyapatite (HA) are examples of materials that can enhance osseointegration by changing the chemistry of the outer surface 28. In other embodiments, the outer surface 28 can comprise macroscopic structures, such as, for example, threads, micro-threads, indentations, and/or grooves that are configured to promote osseointegration and can be used alone or combined with the roughening and/or the coatings described above. In one embodiment, the outer surface 28 comprises a microstructure surface, such as, a highly crystalline and phosphate enriched titanium oxide microstructured surface with open pores in the low micrometer range. An example of such a surface is sold under the trademark, TiUnite™ by Nobel Biocare AB™. In another embodiment, it is particularly advantageous for a zirconium ceramic body can be coated with porous zirconium to provide a microstructure surface. In another embodiment, the microstructure surface can be coated with a substance configured to promote osseointegration (such as BMP).

With particular reference to FIGS. 1B-C, the illustrated connection portion 18a comprises a top surface 21 of the implant 20, which is defined by the proximal end 22 of the implant 20. In the illustrated embodiment, the top surface 21 comprises a substantially flat or planar surface that extends generally perpendicular to a longitudinal axis L of the implant 20. A chamfered edge 23 can extend between the top surface 21 of the implant 20 and the outer surface 28 of the body 26 of the implant 30 with the interface between the chamfered edge 23 and the top surface 21 defining an outer periphery of the top surface 21 and an internal socket 66 defining an inner periphery of the top surface 21. In one arrangement, the outer surface 28 of the implant 20 includes a feature (e.g., enriched titanium oxide surface) configured to promote osseointegration and/or soft tissue integration as described above. In such an embodiment, the feature configured to promote osseointegration and/or soft tissue can also extend onto the top surface 21 and in another embodiment, the feature can substantially cover the entire top surface 21 of the implant 20. However, in other embodiments, the top surface 21 can be formed without any additional features to promote mating and sealing with other components as will be described below.

Figure 1D:
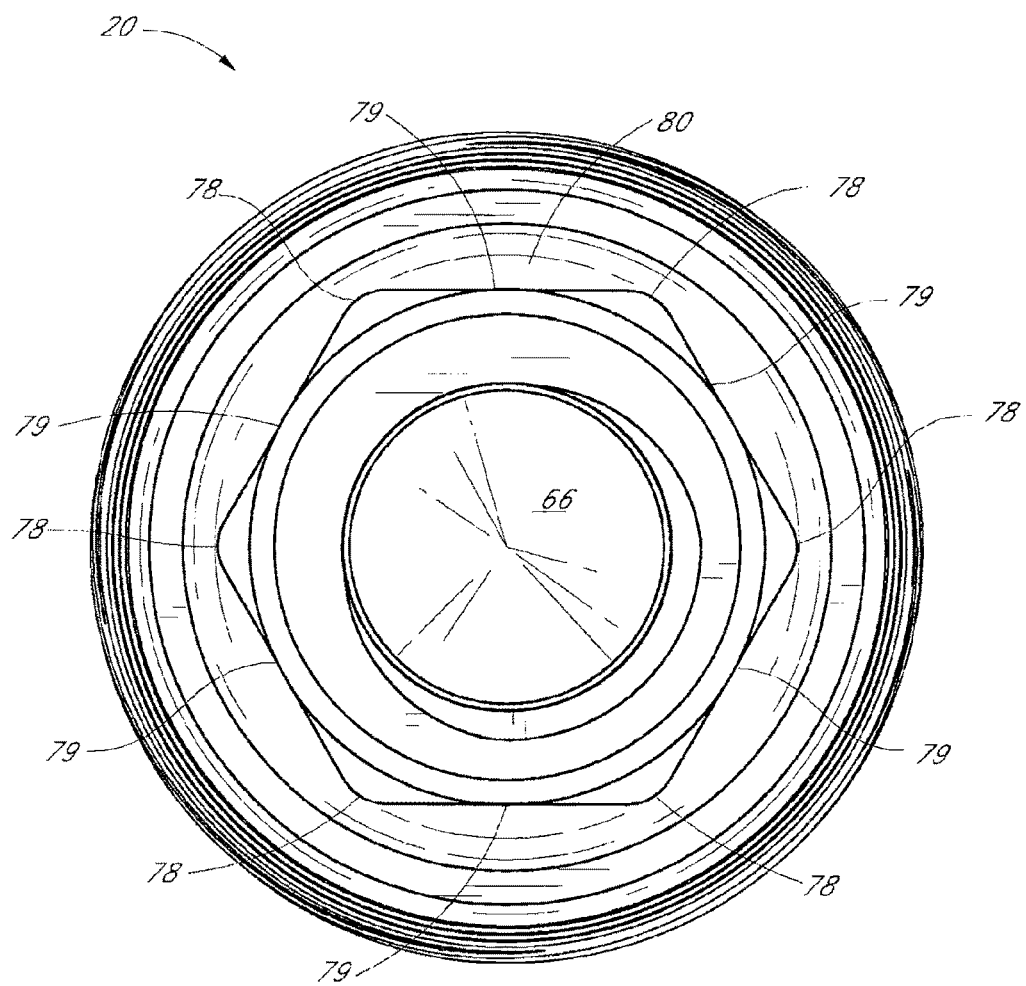
FIG. 1D is a top view of the dental implant of FIG. 1A.

As shown in FIGS. 1B-D, the internal or open socket 66 has an open end in the top surface 21 of the implant 20. In the illustrated arrangement, the socket 66 comprises a substantially conical or tapered portion 68 that is positioned above an interlock recess 74, which is, in turn, positioned above a threaded portion 70 of the socket 66.

With particular reference to FIG. 1C, the tapered portion 68 has a generally conical shape defined by tapering side wall or surface 80 that tapers inwardly with respect to the longitudinal axis L of the implant 20. In the illustrated embodiment, the interlock recess 74, in turn, is defined by a plurality of interconnected substantially flat side walls 79 that form a generally hexagonal recess that has a cross-sectional shape in the form of a hexagon. The flat sides 79 can be interconnected by rounded corners 78 (see FIG. 1D). As will be described below, the interlock recess 74 provides surfaces 79 that resist rotation between the implant 20 and a mating component and/or providing an indexing function to the implant 20. It is anticipated that in modified embodiments the interlock recess 74 can have other configurations, such as, for example, a square, an octagon, and/or various combinations of lobes or recesses.

With particular reference to FIGS. 1C and 1D, in the illustrated arrangement, the generally conical shape of the conical portion 68 and the generally hexagonal shape of the interlock recess 74 can result in the corners 78 and portions of the side walls 70 of the interlock recess 74 extending into a substantial portion of the side wall 80 of the conical portion 68. That is, in the illustrated embodiment, the corners 78 and certain portions of the side walls 79 near the corners 78 will extend further into the conical portion 68 as compared to the portions of the flat sides 79 distanced from the corners 78 of the interlock recess 74. Accordingly, the flat sides 79 of the interlock recess 74 can be configured to extend upwardly for along at least a portion of the conical portion 68. In the illustrated embodiment of FIG. 1C, the flat sides 79 and corners 78 can extend approximately to a midpoint of the conical portion 68. In one embodiment, this interface between the interlock recess 74 and the conical portion 68 can be formed by sequentially forming the conical portion and then the interlock recess 74 (or vice versa) with machining tools. The illustrated arrangement is advantageous in that it results in a smooth transition between the two portions of the socket 66 reducing stress concentrations and risers. In the description below, the portion of the conical portion 68 that includes features of the interlock recess 74 will be referred to as a transition area 71.

As best seen in FIG. 1C, below the interlock recess 74 can be a sub-chamber 77 that is located above the threaded chamber 70 and is defined by a generally cylindrical side wall 84. In the illustrated embodiment, the sub-chamber 77 has a substantially circular cross-section with a diameter that can be slightly larger than the largest extent of the threaded chamber 70. Furthermore, the sub-chamber 77 preferably is relatively short as compared to the interlock recess 74 or the threaded chamber 70. The sub-chamber 77 can be used in conjunction with a tool and will be discussed in greater detail below. The sub-chamber 77 can also be used to provide a transition between the threaded portion 70 and the interlock recess 74, which can facilitate efficient machining of the socket 66. In other embodiments, the sub-chamber 77 can be eliminated.

With continued reference to FIG. 1B-D, the corners 78 of the interlock recess 74 preferably are rounded so as to facilitate machining the socket 66 with machining tools. Thus, in some embodiments, the shape of the interlock portion 75 can be configured such that it can be easily cut by the end of a cylindrical milling bit. However, the shape of the interlock portion 75 can include squared corners in other embodiments. In addition, as mentioned above, the shape of the interlock recess 74 can be modified to other polygon shapes, such as a square shape, an octagonal shape or a triangular shape, or combinations thereof.

The connection portion 18a is advantageously configured to provide an enhanced connection interface and to provide flexibility such that the implant 20 can mate with multiple types of dental components. In particular, as noted above, the conical portion 68 comprises a side wall 80 that tapers inwardly with respect to the longitudinal axis L of the implant 20 providing a wider initial opening 82 for the socket 66. With reference to FIG. 1C, the particular geometry of the conical chamber 68 defines a conical half angle α with respect to the longitudinal axis L. In one embodiment, the conical half angle α is between about 10 degrees and about 20 degrees. That is, the angle between the inner wall 80 and a longitudinal center line L preferably is between about 10 degrees and about 20 degrees. In one embodiment, the conical half angle is about 12 degrees.

As will be described below, the conical portion 68 advantageously provides a tapered mating surface for corresponding tapered parts of a mating component. In this manner, the conical portion 68 can be used to create a tapered fit or connection between the mating component and the dental implant 20. The tapered connection provides an enhanced seal between the mating component and the dental implant 20 preventing bodily fluids and bacteria from entering the socket 66. In addition, the conical portion also advantageously balances the sealing advantages of a tapered connection with the ability to remove, without tools, conical mating parts inserted into the conical chamber 68. The 12 degree conical half angle has been found to provide an improved balance between these advantages.

Another advantage of the illustrated embodiment is the ratio between the length (d1) of the conical portion 68 and the length (d2) the interlock recess 74. With reference to FIG. 1C, in the illustrated arrangement, the ratio of the length of the conical portion 68 with respect to the length of the interlock chamber is about 1:1. In one preferred embodiment, the depth (d1) of the conical portion 68 is at least about 1 mm and the depth (d2) of the interlock recess 74 is at least about 1 mm. As shown in FIG. 1C, the length (d1) of the conical portion 68 is a distance measured in a vertical direction from the top surface 21 of the implant 20 to the portion of the socket 66 in which the tapered surfaces 80 of the conical portion 68 terminate. Accordingly, the length (d1) of the conical portion 68 includes the transition area 71 described above. The length (d2) of the interlock recess 74 is measured in a vertical direction from the end of the conical portion 68 (i.e. excluding the transition area 71) to the end of the interlock recess 74. The ratios and length of the conical portion 68 and the depth and length of the interlock recess 74 advantageously combine the benefits of a sufficiently long tapered connection to provide an effective seal with a sufficiently long interlock recess 74 such that a sufficient driving torque can be transmitted to the implant 20, when the implant is driven into the patient.

In addition, as described above, in the illustrated embodiment, the body 26 of the implant 20 is tapered and includes threads 30. With continued reference to FIG. 1C, in the illustrated embodiment, the interlock region 74 is positioned below (i.e., with respect to the longitudinal axis L of the implant 20) the substantially cylindrical collar 9 of the implant body 26 and the threads 30 extend above (again, with respect the longitudinal axis L) the end of the interlock recess 74. The combination of the tapered body 26 and the deep threads 30 reduce the amount of material available at the proximal end of the implant 20. The above-described arrangement advantageously provides a sealing surface formed by the conical portion 68 and an interlock recess 74 that is sufficiently wall thick to maintain the structural integrity of the body 26. In addition, as described below, the socket 66 also is configured to provide sufficient area at the top surface 21 to support additional components.

Yet another advantage of the illustrated embodiment is an area or thickness of the substantially planar top surface 21 of the implant 20. As will be described in detail below, the top surface 21 of the implant 20 advantageously can provide a surface to support certain dental restorations on the top surface 21 of the implant 20. Additionally or alternatively, the top surface 21 can be used to support a component that bypasses the interlock recess 74. Accordingly, in one embodiment, the top surface 21 of the implant 20 has at least a thickness as measured between the outer and inner periphery of the top surface 21 that is greater than at least 0.2 mm and in another embodiment greater than about 0.25 mm. In one embodiment, the thickness of the top surface 21 is about 0.25 mm.

Figure 2A:
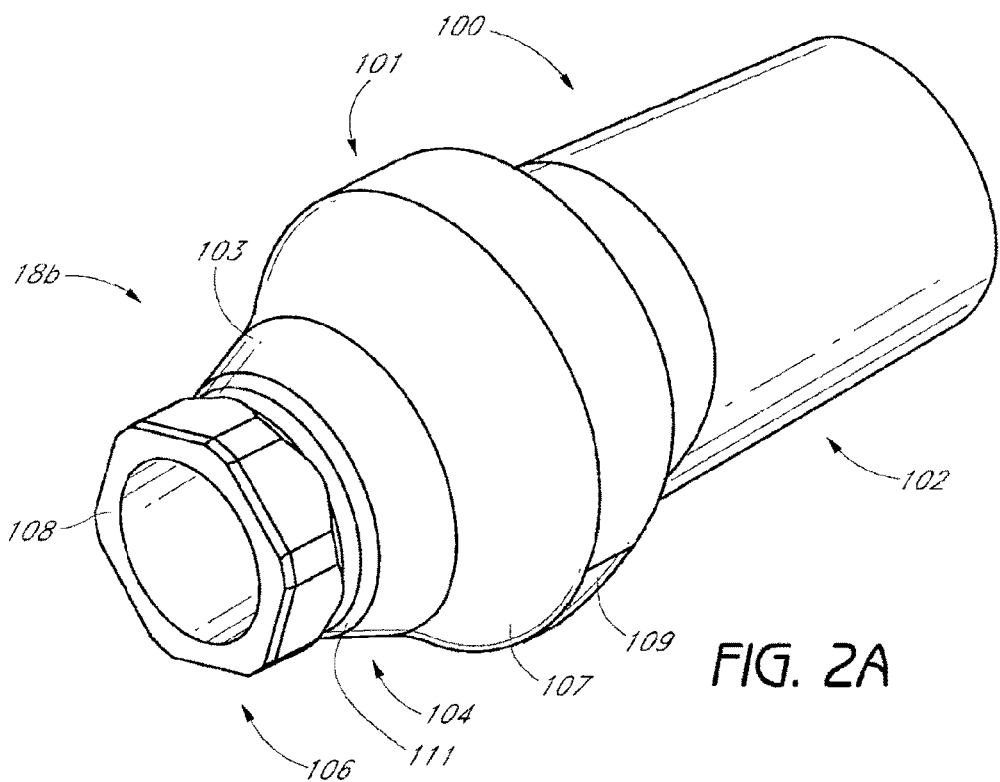
FIG. 2A is a bottom side perspective view of an abutment according to one embodiment of the present invention.
Figure 2B:
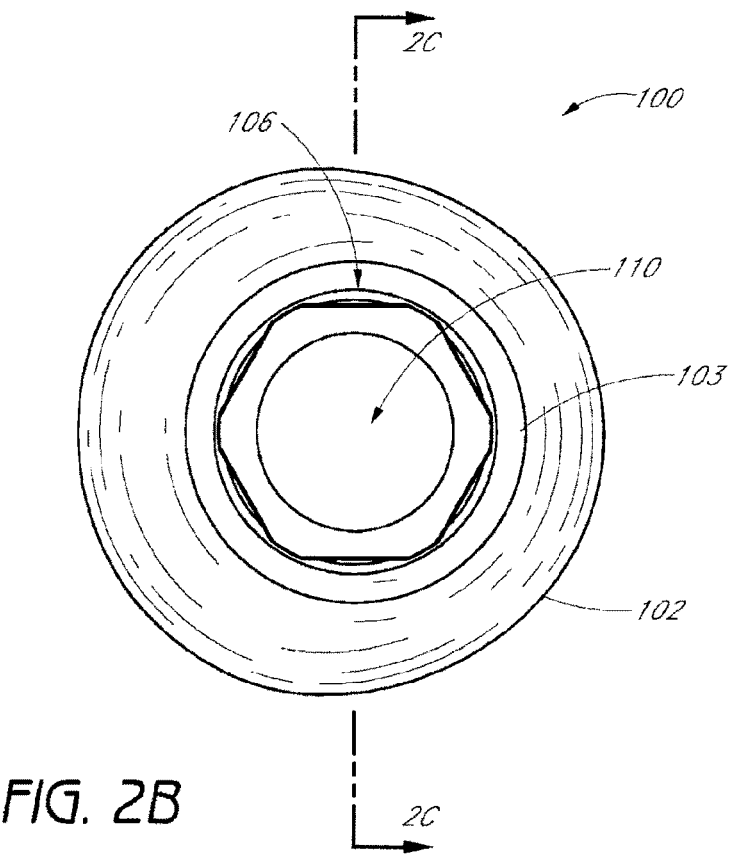
FIG. 2B is a bottom view of the abutment of FIG. 2A.
Figure 2C:
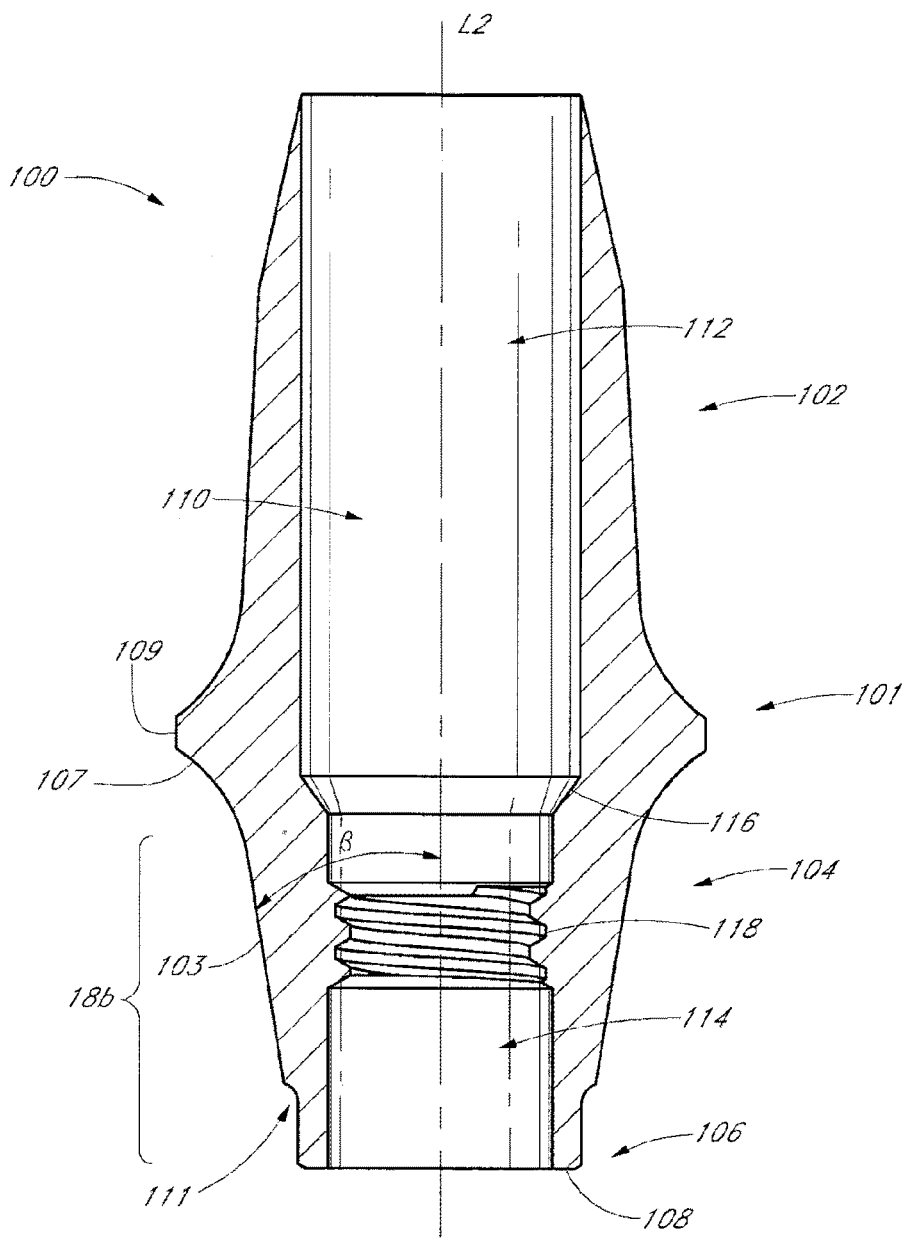
FIG. 2C is a cross-sectional side view taken along line 2C-2C of FIG. 2B.

FIGS. 2A-C illustrate an embodiment of an abutment 100 that includes a connection portion 18b configured to mate with the connection portion 18a of the dental implant 20 described above. As will be explained below, the abutment 100 can be formed as a variety of dental components, such as, for example, a healing cap, impression coping, a temporary healing abutment, or a final abutment, to name a few. The illustrated abutment 100 is configured to serve as a support for a single tooth restoration (e.g., a crown). The abutment 100 is preferably made of dental grade titanium; however, other suitable materials such as various types of ceramics can also be used. In still other embodiments, a combination of materials can be used, for example, dental grade titanium and ceramics.

With reference to FIGS. 2A and 2C, in the illustrated embodiment, the abutment 100 can comprise an upper portion 102 that can be configured to receive the single tooth restoration (not shown). Between the upper portion 102 and connection portion 18b is a waist 101 that comprises a generally outwardly tapering side wall 107 and a generally vertically extending margin 109. As shown in FIGS. 2A and 2B, the side wall 107 and the margin 109 can have a shape configured to generally match the anatomical features of the patient's gum tissues and/or the final restoration. Accordingly, the side wall 107 and the margin 109 can have an asymmetrical cross-section (see FIG. 2B) and/or a varying height (see FIG. 2A).

The connection portion 18b, in turn, can include a conical region 104 generally adjacent the waist 101 and an interlock portion 106 generally positioned at the distal end of the abutment 100. The interlock portion 106 of the illustrated embodiment preferably comprises a shape that can correspond to and/or be sized to fit within the interlock recess 74 of the dental implant 20, the shape of which is best seen in FIG. 1B. For example, in the illustrated embodiment, the interlock portion 106 has a hexagonal shape which can correspond to the shape of the illustrated embodiment of the interlock recess 74 of the implant 20. Nevertheless, as with the interlock recess 74 of the implant 20, the interlock portion 106 can be configured in any variety of shapes, polygonal or otherwise as will be described below.

With continued reference to FIGS. 2A-2C, the conical region 104 of the abutment 100 can be configured to be inserted into the conical portion 68 of the dental implant 20 to form a tapered fit. Accordingly, as with the conical portion 68 of the implant 20, the conical region 104 of the abutment 100 comprises a conical shape comprising a half angle β with respect to a longitudinal axis L2 of the abutment (see FIG. 2C). The half angle β can be between about 10 and 20 degrees and in one embodiment is about 12 degrees. In general, when a sealing arrangement is desired between the conical portion 68 of the implant 20 and the conical region 104 of the abutment 100, the half angles α and β are substantially the same.

With reference to FIGS. 2A and 2C, a rounded waist or narrowed portion 111 can be formed between the conical region 104 and the interlock portion 106 of the abutment 100. The narrowed portion 111 can aid in machining the abutment 100 with machining tools. In other embodiments, the narrowed portion 111 can be eliminated.

As best seen in FIG. 2C, the abutment 100 can include an inner bore 110. The inner bore 110 can extend through the center of the abutment 100 and can be approximately coaxially aligned with the longitudinal center line L2 of the abutment 100. The inner bore 110 can be divided into a first and a second region 112, 114. In some embodiments, the first region 112 can comprise a diameter that is slightly larger than the diameter of the second region 114. In such an embodiment, a seat 116 can be formed between the first and second regions 112, 114. This seat 116 can support a coupling member 200 (see FIGS. 5A and 5B), as described in greater detail below. Further, the second region 114 can be formed to include internal capture threads 118 that are configured to interface with the coupling member 200.

Figure 3A:
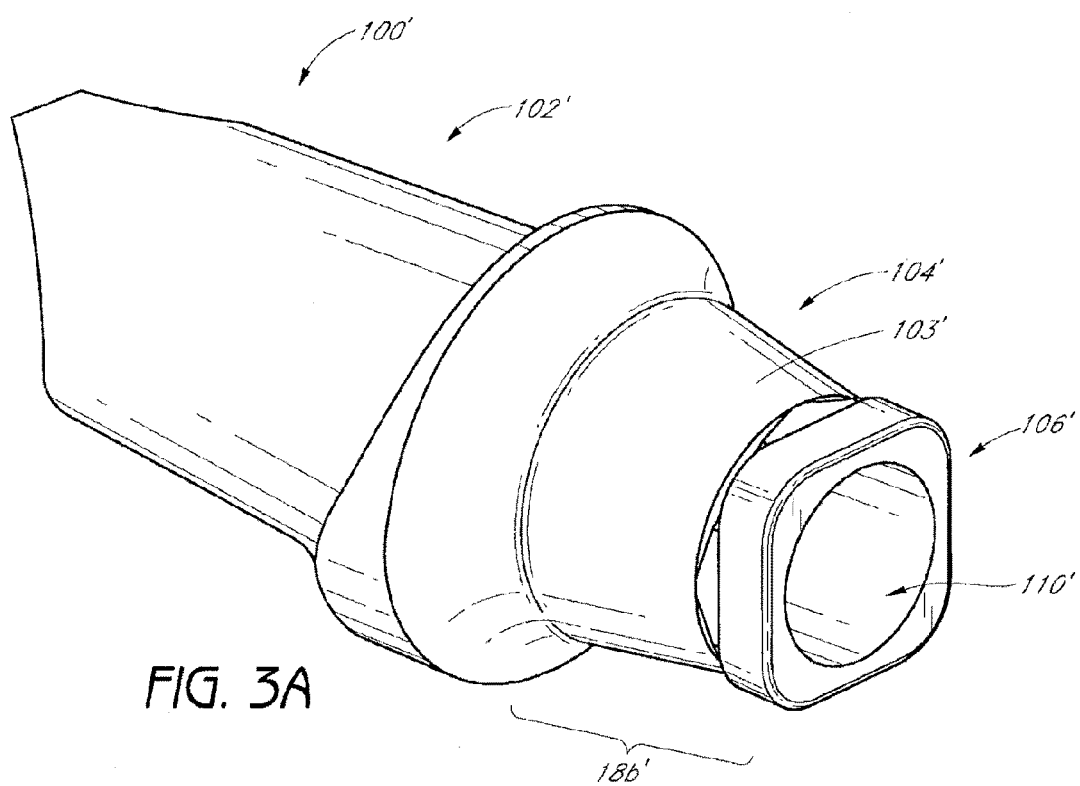
FIG. 3A is a bottom side perspective view of another embodiment of an abutment.
Figure 3B:
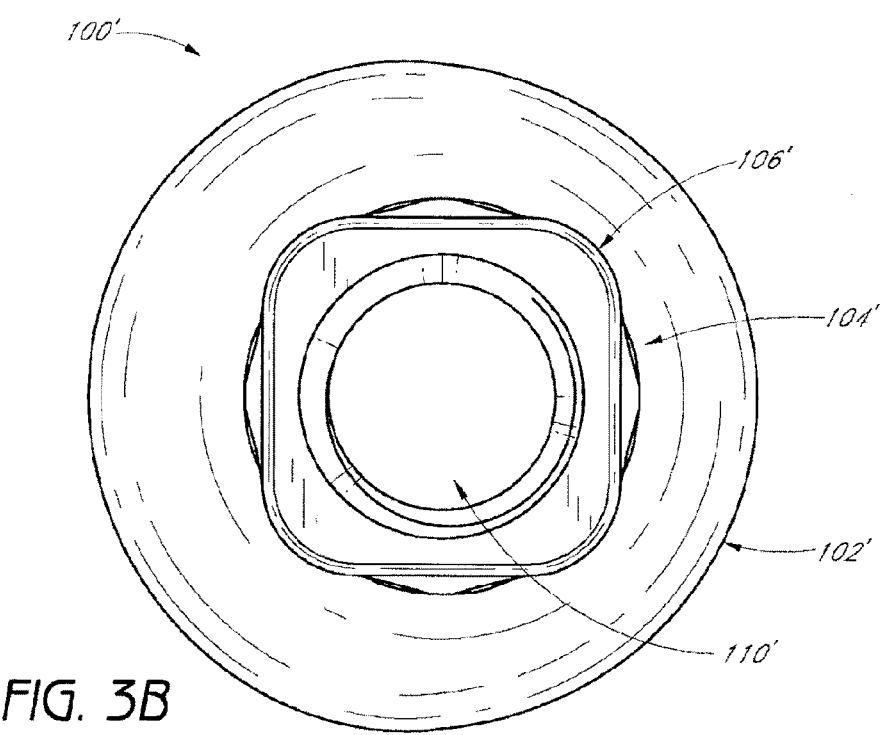
FIG. 3B is a bottom view of the abutment of FIG. 3A.
Figure 4A:
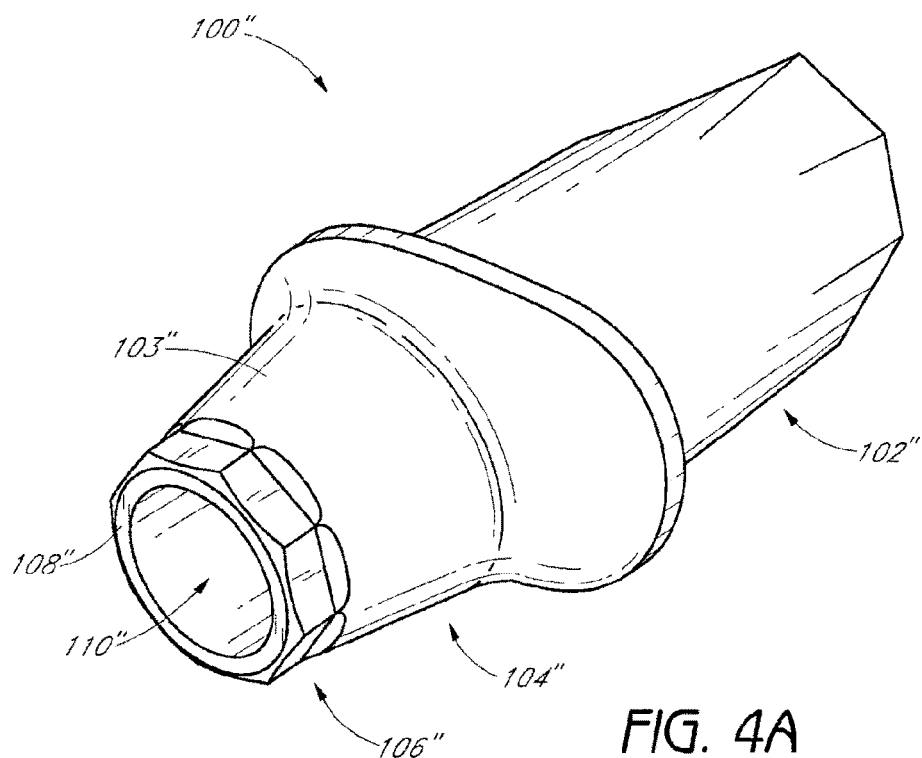
FIG. 4A is a perspective view of an abutment according to one embodiment.
Figure 4B:
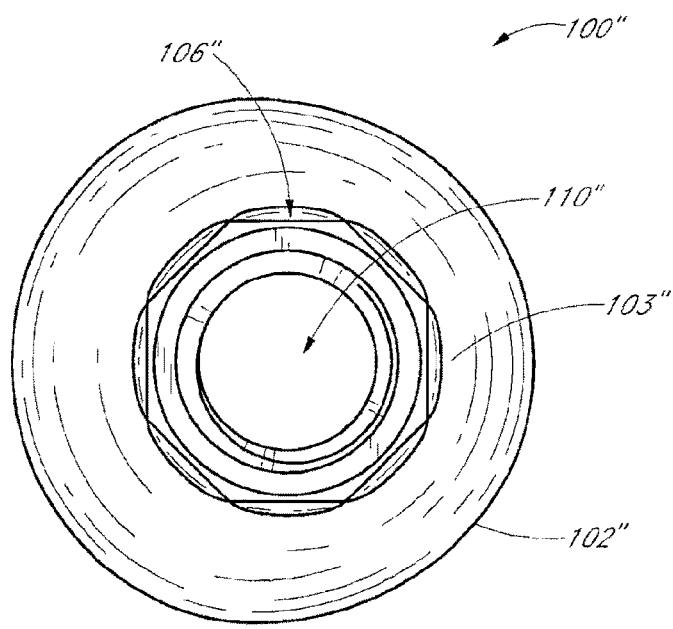
FIG. 4B is a bottom view of the abutment of FIG. 4A.

As mentioned above, the interlock portion 106 and the corresponding interlock recess 74 of the implant 20 can be configured in a variety of different manners. For example, FIGS. 3A and 3B illustrate an embodiment in which the interlock portion 106' has a generally square shape with four flat sides and rounded edges. The interlock recess 74 of the implant (not shown) can have a corresponding similar shape for receiving the interlock portion 106' of the abutment 100'. FIGS. 4A and 4B illustrate another embodiment of an abutment 100" in which the interlock portion 106" has an octagonal shape comprising eight flat sides. In one embodiment, the abutment 100" of FIGS. 4A and 4B can be configured to mate with a corresponding octagonal shaped interlock portion of an implant (not shown). In another embodiment, the abutment 100" can be configured to mate with a square shaped interlock portion as described with reference to FIGS. 3A and 3B. Such an arrangement can provide the additional advantage in that additional rotational positions for the abutment 100" relative to the dental implant 20 are provided. That is, when connection portion 18b is to be inserted into the connection portion 18a of the dental implant 20, a polygon shape of the interlock portion 106, for example an octagonal shape, allows the abutment 100 to have eight possible rotational positions relative to the dental implant 20 with a square shaped interlock portion. This can allow the relative rotational position of the abutment 100 to be tuned to the desirable rotational position when installed with the dental implant 20. The same principle can be extended to the hexagonal interlock recess 74 and interlock portion 106 of FIGS. 1A-2C by providing the interlock region with, for example, ten sides.

FIGS. 5A and 5B illustrate an embodiment of a coupling screw 200 that can be used to mechanically couple the abutment 100 to the implant 20. The coupling screw 200 can be made of dental grade titanium alloy, although other suitable materials can be used, such as various other metals or ceramics. The coupling screw 200 can be sized and shaped to extend through the inner bore 110 of the abutment 100 and into the socket 66 of the implant 20. The coupling screw 200 can include an externally threaded lower region 202 that can engage the internal capture threads 118 of the abutment 100 and can engage the threaded chamber 70 of the implant 20. The threads 204 of the coupling screw 200 can engage the capture threads 118 so that the coupling screw 200 does not become disassociated as the abutment 100 is transferred and lifted into a patient's mouth.

The coupling screw 200 also preferably includes a recess 206 for receiving a correspondingly shaped tool to facilitate installation and removal of the coupling screw 200 from the implant 20. The recess 206 can be located on a top surface 208 of the screw 200. In the illustrated embodiment, the recess 206 is in a shape configured to receive a Unigrip® rotational tool provided by Nobel Biocare™. In other embodiments, the recess 208 can have a different shape, such as, for example, a hexagon configured to allow for the insertion of a hexagonally shaped tool such as a conventional Allen® wrench to install or remove the coupling screw 200 from the implant 20.

Figure 6:
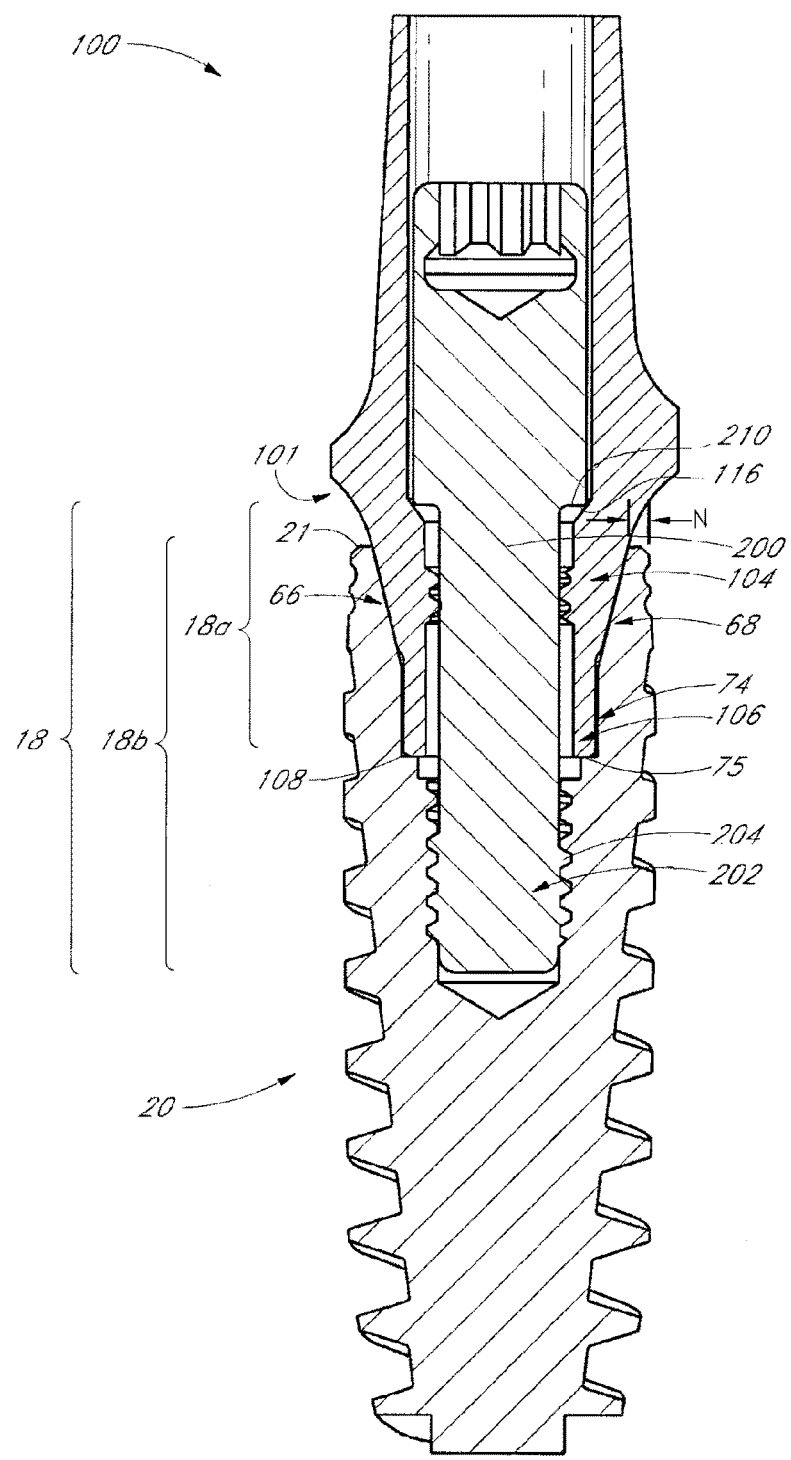
FIG. 6 is a cross-sectional side view of the implant of FIG. 1A and the abutment of FIG. 2A attached together with the coupling element of FIG. 5A.

FIG. 6 illustrates an embodiment wherein the abutment 100 has been coupled to the dental implant 20 with the coupling screw 200 via the connection 18. As illustrated, the interlock portion 106 of the abutment 100 preferably is aligned and inserted into the interlock recess 74 of the dental implant 20. Furthermore, the conical region 104 of the abutment 100 preferably is inserted into the conical portion 68 of the dental implant 20 to form a sealed or tapered fit connection between the abutment 100 and the implant 20. The abutment 100 can be inserted into the socket 66 of the dental implant 20 such that the lower end 108 of the interlock portion 106 is in contact with the lower end 75 of the interlock recess 74. As used in this application, a sealed or taper fit refers to the interface and between contacting tapered surfaces of the conical portion 68 of the implant 20 and the conical region 104 of the abutment 100 or other mating component. As is known in the art, a tapered fit between tapered surfaces can provide a particularly strong and efficient seal between mating components that can prevent or substantially inhibit the migration of tissue and/or fluids between the interface between the mating components and into the socket 66. Although the illustrated embodiments show conical components with generally circular cross-sections it should be appreciated that in modified embodiments, the tapered surfaces can be provided by non-circular structures such as polygons with tapered flat sides, ovals, and/or complex shapes.

With continued reference to FIG. 6, the lower threaded region 202 of the coupling screw 200 can be engaged with the threaded chamber 70 of the dental implant 20. The seat 210 of the coupling screw 200 can also abut the seat 116 of the abutment 100. This engagement of the coupling screw 200 and the abutment 100 and the dental implant 20 can thereby secure the abutment 100 to the dental implant 20.

As mentioned above, the tapered fit or connection between the abutment 100 component and the dental implant 20 advantageously provides an enhanced seal between the abutment 100 and the dental implant 20 preventing bodily fluids and bacteria from entering the socket 66. In addition, the ratios between depth and length of the conical portion 68 and the depth and length of the interlock recess 74 advantageously combines the benefits of a tapered connection with a sufficiently long interlock recess 74 to provide sufficient resistance to rotation of a mating component.

Another advantage of the illustrated embodiment is that the abutment 100 does not sit on the top surface 21 of the implant 20. Instead, the tapered waist 101 extends from the interface between the top surface 21 and the opening of the socket 66. This arrangement advantageously results in a reduction of the width (i.e., in a direction substantially perpendicular to the longitudinal axis of the implant 20) of the implant platform from the perimeter of the top surface 21 to the portion of the abutment 100 emerging from the socket 66. This reduction of size indicated by the arrow N-N in FIG. 6 forms a waist or narrowed portion in the structure of the implant 20 and abutment 100 combination that has a maximum width (as measured in a direction perpendicular to the longitudinal axis of the implant 20) that is approximately equal to the width of the top surface 21 of the implant. The waist can increase the volume of soft tissue, and blood supply to soft tissue, around the implant and abutment connection promoting gingival health and beauty.

Figure 7A:
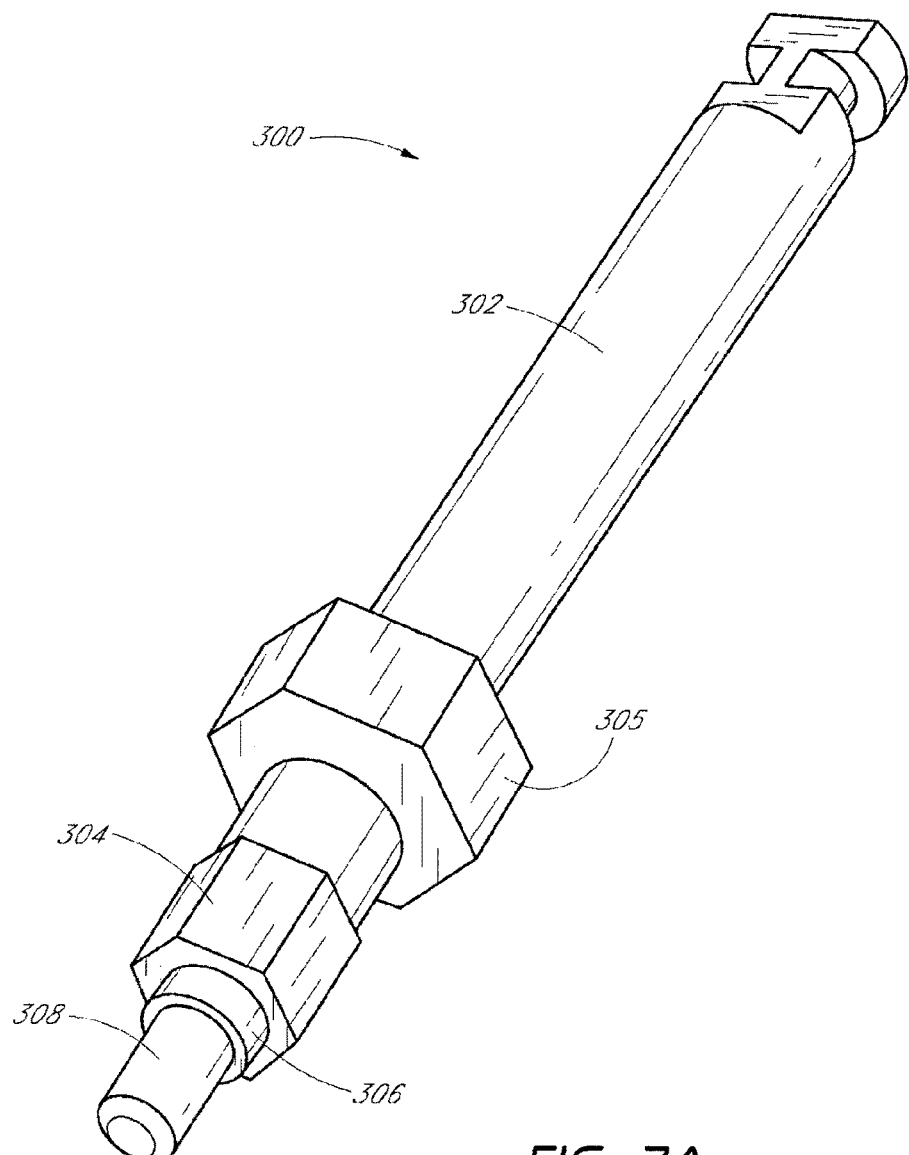
FIG. 7A is an embodiment of an insertion tool that is configured to interface with the dental implant of FIG. 1A.

FIG. 7A illustrates a dental tool 300 that can be used to drive the dental implant 20 into a patient. The dental tool 300 can comprise a shank portion 302, which in some embodiments can be connected to a rotary machine (not shown). A drive portion 304 can be formed at the front end of the tool 300, and can comprise a polygon shaped cross-section configured to mate with the interlock recess 74 of the implant 20. In the particular embodiment illustrated in FIG. 7A, the drive portion 304 has a hexagonal shape. In another embodiment configured to mate with the implant of FIGS. 1A-D, the drive portion 304 can be configured to have a square shape (not shown). Of course, the drive portion 304 can have a variety of other shapes and can be configured to transmit torque through the interlock recess 74 to the implant 20.

Figure 7B:
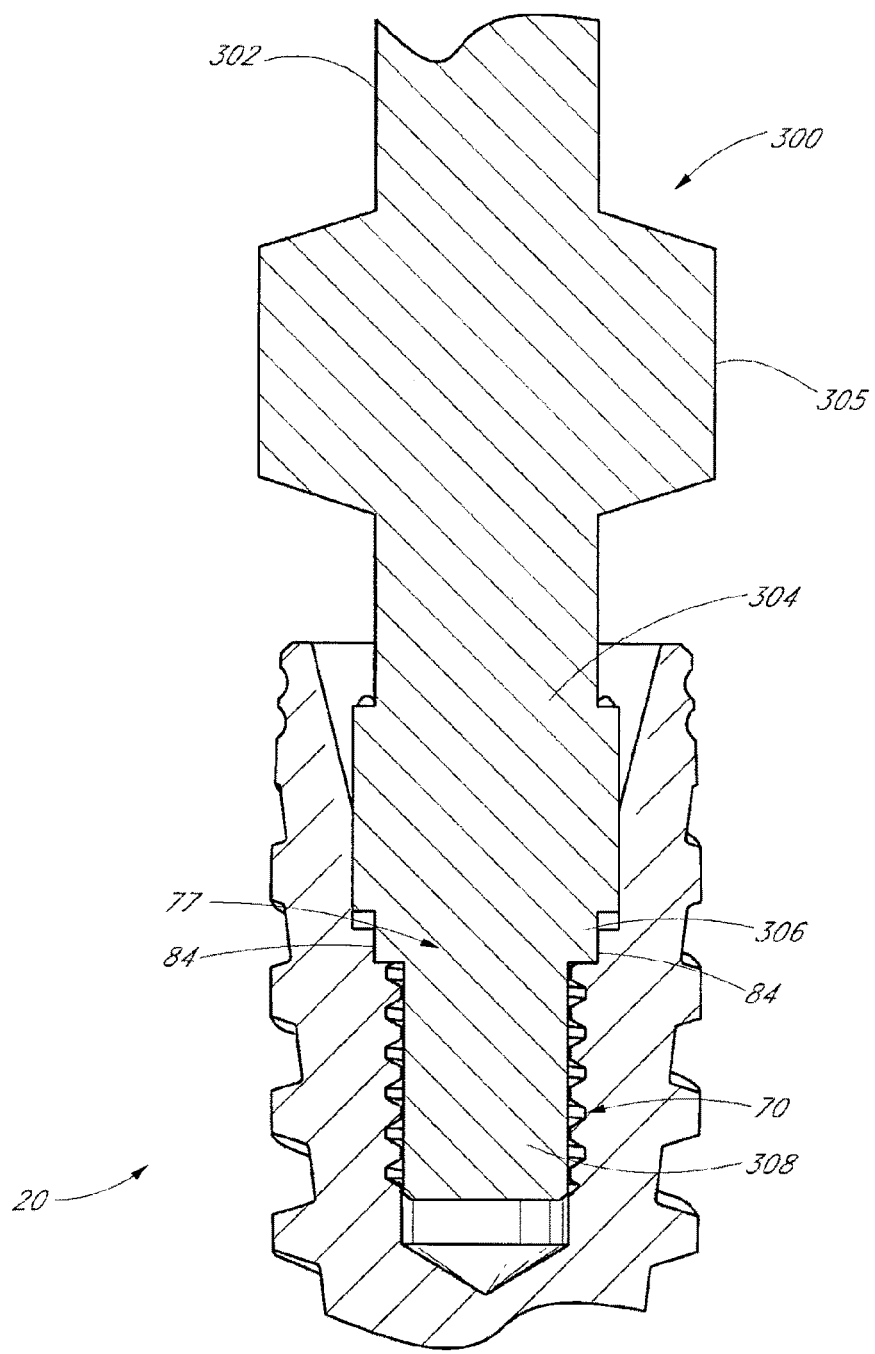
FIG. 7B is an enlarged cross-sectional side view of the dental implant of FIG. 1A interfaced with the insertion tool of FIG. 7A.

With continued reference to the embodiment of the tool 300 illustrated in FIG. 7A, a cylindrical portion 306 can be formed below the polygon shaped portion 304. The cylindrical surface 306 preferably tapers towards the front end of the dental tool 300 and is configured to be inserted into the sub-chamber 77 of the dental implant 20, as shown in FIG. 7B. When the dental tool 300 is inserted into the dental implant 20, the portion 306 preferably wedges into the sub-chamber 77 producing a friction fit so that the implant 20 can be lifted and carried by the dental tool 300. That is, the dental tool 300 can simply be firmly inserted into the dental implant 20 to cause frictional engagement between the dental tool 300 with the dental implant 20 to temporarily connect the dental tool 300 and dental implant 20. Thus, the dental tool 300 can be used to lift and place the dental implant 20 into a desired position.

With continued reference to FIG. 7A and FIG. 7B, the tool 300 also preferably comprises a thread guide portion 308 that preferably is circular in cross-section and is configured to be inserted into the threaded chamber 70 of the dental implant 20. The diameter of the threaded guide portion 308 is preferably smaller than the smallest diameter defined by the threads of the threaded chamber 70. The tool 300 can also include a manual tool engagement section 305 positioned along the shaft 302 and configured to engage a manual torque applying tool (e.g., a wrench).

FIG. 7C is a distal end of a modified embodiment of the tool 300 described above. In this embodiment, the tool 300 includes a drive portion 304 and a shank portion 302, a thread guide portion 308 and tool engagement section 305 as described above. However, in this embodiment the cylindrical surface 306 is replaced by a clip engagement member 310, which comprises an annular ridge 312 positioned on the guide portion 308. Between the ridge 312 and the drive portion 304, an elastic clip or ring (see FIG. 7D) can be positioned. In one embodiment the clip 316 is made of a polyketone (e.g., PEEK) or another elastic material. Once in position, the clip 316 can have a diameter slightly larger than the ridge 312. In this manner, the clip can be positioned within the sub-chamber 77 to form an elastic fit that allows the tool 300 to grip and hold the weight of the implant 20.

As discussed above, the components configured with the implant 20 can be variously configured. For example, FIGS. 8A and 8B illustrate two different embodiments of an abutment 400, 400' configured to mate with the implant 20 described above and to bypass the connection with the interlock recess 74 of the implant 20. The abutments 400, 400' of FIGS. 8A and 8B can be termed "healing" abutments, which can be used after the implant 20 is initially implanted into the patient's alveolar bone. In such situations, it may be advantageous to avoid loading the implant 20 with stresses and other forces while the implant 20 osseointegrates with the alveolar bone to form a tight bond with the implant 20 and/or to shape the contours of the soft tissue surrounding the implant 20.

In the illustrated embodiment of FIG. 8A, the abutment 400 can include a threaded section 402 that is configured to mate with the threaded chamber 70 of the implant 20. The abutment 400 can also include an intermediate section 404. The intermediate section 404 can have a substantially conical and/or tapered shape configured to fit within the conical portion 68 of the implant 20. However, the size of the intermediate section 404 is preferably configured such that it smaller than the conical portion 68 and does not engage the conical portion 68 in a tapered fit when the threaded section 402 engages the threaded chamber 70. For example, the intermediate section 404 can have a clearance fit with the conical portion 68 of the implant 20. The intermediate section 404 can aid the abutment 400 in being generally centered when received into the implant 20. As will be explained below, a top cover 410 of the abutment 400 can engage the top surface 21 of the implant. Thus, the abutment 400 can engage the top surface 21 of the implant 20 while bypassing a tapered fit with the conical portion 68 and while bypassing the interlock recess 74 of the implant 20. Thus, the intermediate section 404 is generally configured to provide a "slip fit" between the abutment 400 and the conical portion 68. As used herein, slip fit refers to a relationship between parts in which conical portion 68 constrains movement of the intermediate section 404 but still provides a gap such that a seal is not formed between the two components. Thus, in other embodiments, the intermediate section 404 can have a non-round cross-sectional and/or can have a tapered, cylindrical or generally non-vertical side walls. In modified embodiments, the abutment 400 can be configured to engage the interlock recess 74 and in such embodiments, the abutment 400 can be coupled to the implant 20 via a coupling screw (not shown).

As also shown in FIG. 8A, the abutment 400 can include a cover portion 410 defining a top height 412. The top height 412 can be defined as the distance from the proximal end of the implant 20 to a top end 414 of the abutment 400 when the abutment 400 is fully seated or received within the receiving chamber 68 of the implant 20. In the illustrated embodiment, when such an embodiment is seated in the receiving chamber 68 of the implant 20, it is contemplated that the cover portion 410 may be the only portion of the abutment 400 that protrudes from the implant 20. In this regard, the cover portion 410 can be configured to act as a temporary prosthesis that covers and protects the interior of the implant 20 while the bone and the implant 20 become set after initial implantation. Thus, the cover portion 410 can be shaped to cover the entire opening of the receiving chamber 68. For example, the cover portion 410 can be substantially cylindrical and have a substantially circular cross-section that generally matches the shape of the posterior end of the implant 20. The cover portion 410 can be configured to rest on top of the implant 20 or can be partially nested within the receiving chamber 68. In the illustrated embodiment, the cover portion 410 is configured to cover and protect the entire top surface 21 of the implant 20. Such an abutment is advantageous when the implant 20 is to be used to support a component that will rest upon the top surface 21 such as an implant supported bridge of abutment because the abutment 400 prevents or inhibits bone tissue growth onto the top surface 21 of the implant. As shown by the dashed lines in FIG. 8A, the height 412 can be increased and in one embodiment the top end can be configured to extend through the soft tissue of the patient. In such an embodiment, the abutment 400 can also be used to guide tissue growth. In the illustrated embodiment of FIG. 8A, the cover portion 410 is configured to lie underneath the soft tissue. Of course, other heights of the cover portion 410 can be used also in other embodiments.

As shown in FIG. 8B, in another embodiment, the abutment 400' can include a threaded portion 402', a intermediate section 404', and a top portion 410' defining a top height 412' measured from a top end 414' thereof to the proximal end of the implant 20 when seated in the implant 20. As with the embodiment of FIG. 8A, the top height 412' can be varied. In this embodiment, the intermediate section 404' is configured to engage the conical portion 68 of the implant 20 in a sealed or tapered fit. Accordingly, the angle intermediate portion can be similar to the abutment 100 described above. The abutment 400' of this embodiment does not cover the top surface 21 of the implant 20 but does engage the conical portion 68 in a sealed or tapered fit. The height 412' can be varied. In one embodiment, the height 412' can be great enough such that the abutment 400' extends through the soft tissue and in another embodiment, the height 412' can be small enough such that the abutment lies beneath the soft tissue. The abutment 400' of FIG. 8B is particularly useful in applications when implant 20 is to be used in combination with an abutment 100 and/or to be used to support a single restoration. In modified embodiments, the abutment 400' can be configured to engage the interlock recess 74 and in such embodiments, the abutment 400 can be coupled to the implant 20 via a coupling screw (not shown).

Although not illustrated, it should be understood that the top surfaces of the abutments of FIGS. 8A and 8B can be provided with a recess (or protrusion) for mating with a torque applying tool. For example, in one embodiment, the abutments 400, 400' include a recess having a shape configured to receive a Unigrip® rotational tool provided by Nobel Biocare™. This recess can be formed similarly to the recess 206 shown above in the embodiment of the coupling screw 200 illustrated in FIGS. 5A-B.

Figure 9:
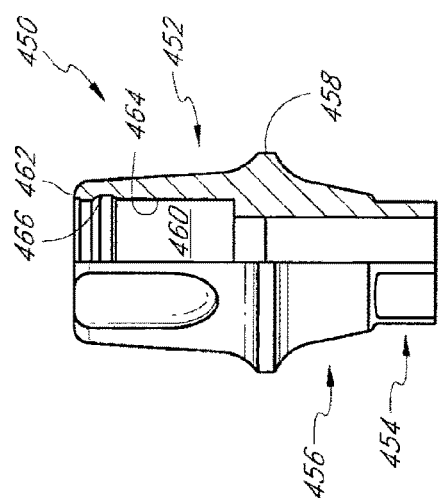
FIG. 9 is a side view of another embodiment of an abutment that can be inserted into the implant of FIG. 1A.

FIG. 9 is a side view of another embodiment of an abutment 450 that can be inserted into an implant, as illustrated in FIGS. 1A-D. The abutment 450 shown in FIG. 9 can be configured to be used with other types of components, and in particular, can be used with a temporary coping, a healing cap, and/or an impression coping as described further below. These features, and others, are described in Applicant's co-pending application Ser. No. 10/748,869 (U.S. Publication No. 2004-0241610), filed on Dec. 30, 2003, entitled "DENTAL IMPLANT SYSTEM", the entirety of which is incorporated herein by reference.

The embodiment of the abutment 450 shown in FIG. 9 includes an upper region 452, an interlock portion 454 generally positioned at the distal end of the abutment 450, and a conical region 456 generally adjacent a waist 458. The upper region 452 is dimensioned and configured to mate with one of a variety of components. Such components can include, for example, those shown in FIGS. 10A-12B. The interlock portion 454 of the illustrated embodiment preferably comprises a shape that can correspond to and/or be sized to fit within the interlock recess 74 of the dental implant 20, the shape of which is best seen in FIG. 1B. For example, in the illustrated embodiment, the interlock portion 454 has a hexagonal shape which can correspond to the shape of the illustrated embodiment of the interlock recess 74 of the implant 20. Nevertheless, as with the interlock recess 74 of the implant 20, the interlock portion 454 can be configured in any variety of shapes, polygonal or otherwise, as described herein. Further, as described above with respect to the abutment 100 of FIGS. 2A-C, the conical region 456 of the abutment 450 can be configured to be inserted into the conical portion 68 of the dental implant 20 to form a tapered fit. Accordingly, as with the conical portion 68 of the implant 20, the conical region 456 of the abutment 450 can comprise a conical shape comprising a half angle, which can be variously configured, as described above with respect to the abutment 100.

As shown in FIG. 9, the abutment 450 can have an open socket 460 that opens into a top surface 462 of the abutment 450. The open socket 460 includes an inner surface 464 that can include an annular groove 466, which, as will be described below, can be used to engage a snapping element of a mating component.

Figure 10B:
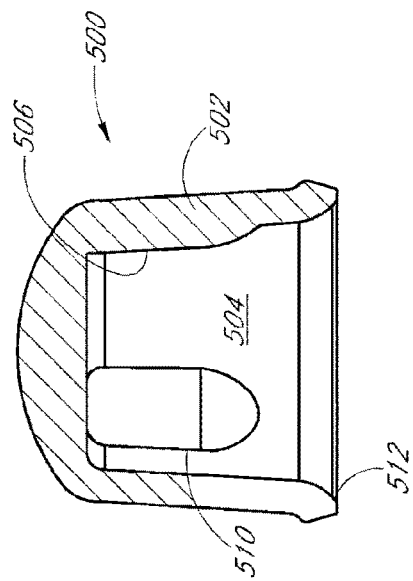
FIG. 10B is a cross-sectional side view of the temporary coping of FIG. 10A.
Figure 10A:
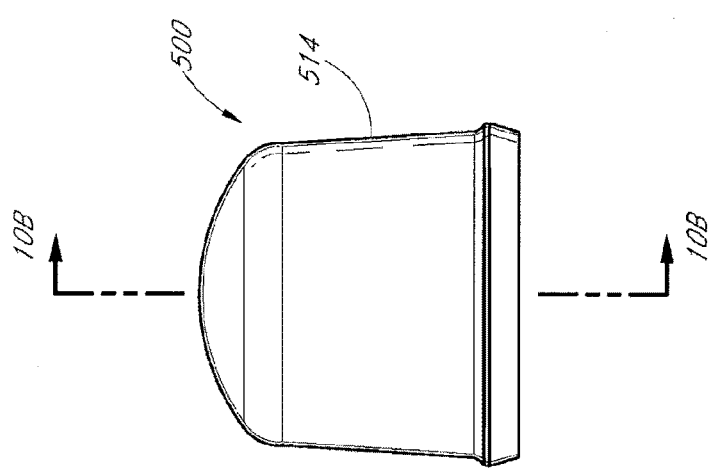
FIG. 10A is a side view of an embodiment of a temporary coping that can be fitted onto the abutment illustrated in FIG. 9.

FIGS. 10A and 10B are a side view and cross-sectional view, respectively, of an embodiment of a temporary coping 500 that can be fitted onto the abutment 450 illustrated in FIG. 9. As explained in greater detail in the above-mentioned co-pending application Ser. No. 10/748,869, the temporary coping 500 or healing cap can help to control the healing and growth of the patient's gum tissue around the implant site. The illustrated embodiment of the coping 500 can therefore be used in combination with the dental implant 20 and the abutment 450 described above. The coping 500 can comprise a body 502 made of a synthetic polymer, such as, for example, polyester or Nylon. However, it should be appreciated that other suitable materials may also be used. The coping 500 can have an outer surface 514 that is preferably white or close to natural tooth color, so that it has a natural appearance when it is placed in the patient's mouth.

The coping 500 can be at least partially hollow and include an inner surface 506 which defines an internal cavity 504. The internal cavity 504 can be sized and dimensioned such that the coping 500 fits over the upper region 452 of the abutment 450. The inner surface 506 can include a stop 512 for limiting the advancement of the coping 500 onto the abutment 450, such as, a base surface that is sized and dimensioned to rest against a flanged portion or waist 458 of the abutment 450. In some embodiments, the coping 500 can be configured to be snap fit onto the abutment 450, and in other embodiments, the coping 470 can be configured such that it can be secured to the abutment 450 via a cap screw that can be inserted through an aperture in the coping 470. The inner surface 506 can include an anti-rotational feature 510 that mates with the abutment 450. Other features and embodiments can be formed by one of skill given the present disclosure.

Figure 11B:
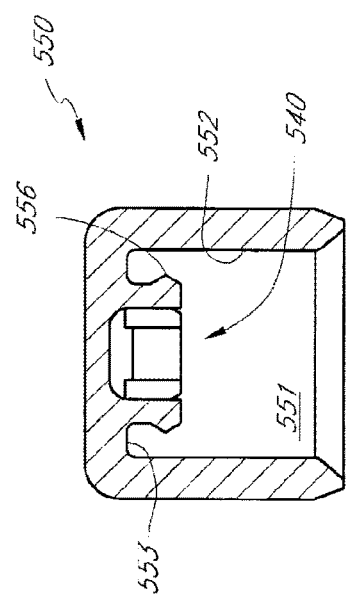
FIG. 11B is a cross-sectional side view of the temporary coping of FIG. 11A.
Figure 11A:
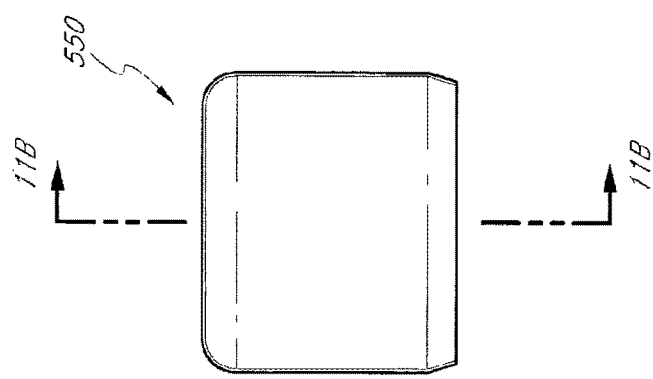
FIG. 11A is a side view of an embodiment of a healing coping that can be fitted onto the abutment illustrated in FIG. 9.

FIGS. 11A and 11B are side and cross-sectional views of temporary healing cap 550 that can be coupled to the abutment 450 of FIG. 9. Additional details of the healing cap can be found in U.S. Patent Publication No. 2006-0228672, which is U.S. patent application Ser. No. 11/377,259, filed on Mar. 16, 2006, the entirety of which is hereby incorporated by reference herein. The healing cap 550 can include an inner cavity 551 defined by an inner surface 552 such that the healing cap 550 can be fitted over the abutment 450 described above. Descending from a top surface 553 of the inner cavity 551 can be a snapping element 554 comprising one or more deflectable prongs 556 configured to engage the groove 466 of the abutment 450 in a snap fit. Additional details and modified embodiments of the snapping element will be described below with respect to the component of FIGS. 12A and 12B.

Referring now to FIGS. 12A and 12B, there is shown a perspective side and cross-sectional view of an embodiment of an impression coping or cap 120 that can be fitted onto the abutment 450 illustrated in FIG. 9. The impression cap 120, can be used to take an impression of the dental implant 20, as described in the above-mentioned U.S. Patent Publication No. 2006-0228672, the entirety of which is incorporated by reference herein.

The illustrated impression cap 120 comprises a body 122 with a proximal end 124 and a distal end 126. The body 122 is preferably made of resilient moldable plastic and/or polymer, such as, for example, polycarbonate. The body 122 defines an inner surface 128, which forms an inner cavity 130. The inner cavity 130 is configured such that the impression cap 120 can fit over the upper region of the abutment 450. The inner surface 128 comprises a side wall 134 and roof 136.

The impression cap 120 is preferably configured to engage the abutment 450. Specifically, the impression cap includes a complementary engagement feature 132, which can be configured to correspond to anti-rotational features on the abutment 450. In the illustrated embodiment, the impression cap 120 engages the abutment 450 in a snap fit that is achieved by providing the cap 120 with a plurality of resiliently deflectable prongs 150 with protrusions 152 configured to engage the recess 466 of the abutment 450. Of course, as mentioned above, those of skill in the art will recognize other configurations for providing a snap fit between the two components. For example, the cap 120 may include a recess positioned on a post configured to engage a protrusion formed on the socket 460 of the abutment 450. In addition, the cap 120 can be configured for friction and/or interference fits.

The impression cap 120 preferably includes one or more embedment features 160. The embedment features 160 facilitate the gripping and retention of the impression cap 120 within an impression tray. The one or more embedment features preferably define at least one interference surface 162, having faces that lie generally transverse to a longitudinal axis of the impression cap. In the illustrated embodiment, the embedment feature 160 comprises one or more flanges 166. In certain embodiments, the flange(s) 166 may include a plurality of through holes 168, which extend through the four corners of the flange 166.

A plurality of elongated protrusions 180 are formed on the side wall and are sized to engage the groove 466 in the abutment 450 when the impression cap 120 is positioned thereon. The protrusions 180 and grooves 51 thus mate to substantially prevent the rotation of the impression cap 120 relative to the abutment 450.

The impression cap 120 has angled surfaces 182 at the proximal end 124 that are configured to abut against the flared portion 45 of the implant 10 when the impression cap 120 is positioned thereon. It should be appreciated that, although the illustrated embodiments of the implant, abutment, healing cap, and impression cap have round cross-sections, in modified arrangements the cross-sections of one or more of these components can be can be non-round.

Figure 13B:
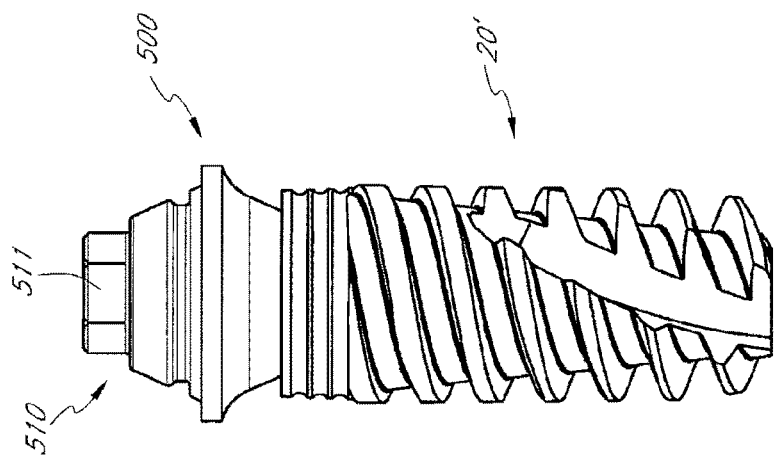
FIG. 13B is a side view of the abutment of FIG. 13A inserted into the implant of FIG. 1A.
Figure 13A:
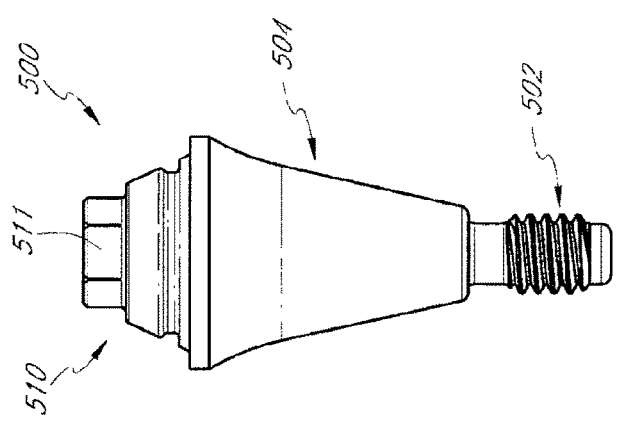
FIG. 13A is a side view of another abutment according to yet another embodiment.

FIG. 13A is a side view of another embodiment of an abutment 500. The abutment 500 can include a threaded portion 502 and a conical portion 504. As noted above with respect to the embodiment of the abutment 400, the abutment 500 can be configured such that the threaded portion 502 can mate with the threaded chamber 70 of the implant 20. The conical portion 504 of the abutment 500 can be configured to be substantially conical and/or tapered. In some embodiments, the conical portion 504 can be complimentarily shaped to form a tapered or sealed fit with the conical portion 68 of the socket 66. Further, the top portion 504 can aid the abutment 500 in being generally centered when received into the implant 20.

As also shown in FIG. 13A, the abutment 500 can include a top surface 510 that includes a hexagonal protrusion 511, that can be used to rotate the abutment 500 such that the threaded portion 502 engages the implant 20. The abutment 500 provides the "stepping down" feature and advantages described above by providing a waist that emerges from the top surface of the implant 20 and thereby exposing the top surface 21 of the implant 20. FIG. 13B illustrates how the abutment 500 can be seated within the implant 20' and can therefore facilitate a "stepping down" connection between the implant 20'. Various screw and/or cement retained restorations (not shown) or other components can be coupled to the top of the abutment 500 as is known in the art. Accordingly, the abutment 500 can include a threaded socket (not shown) that opens at the top of the abutment 500.

Figures 14A, 14B:
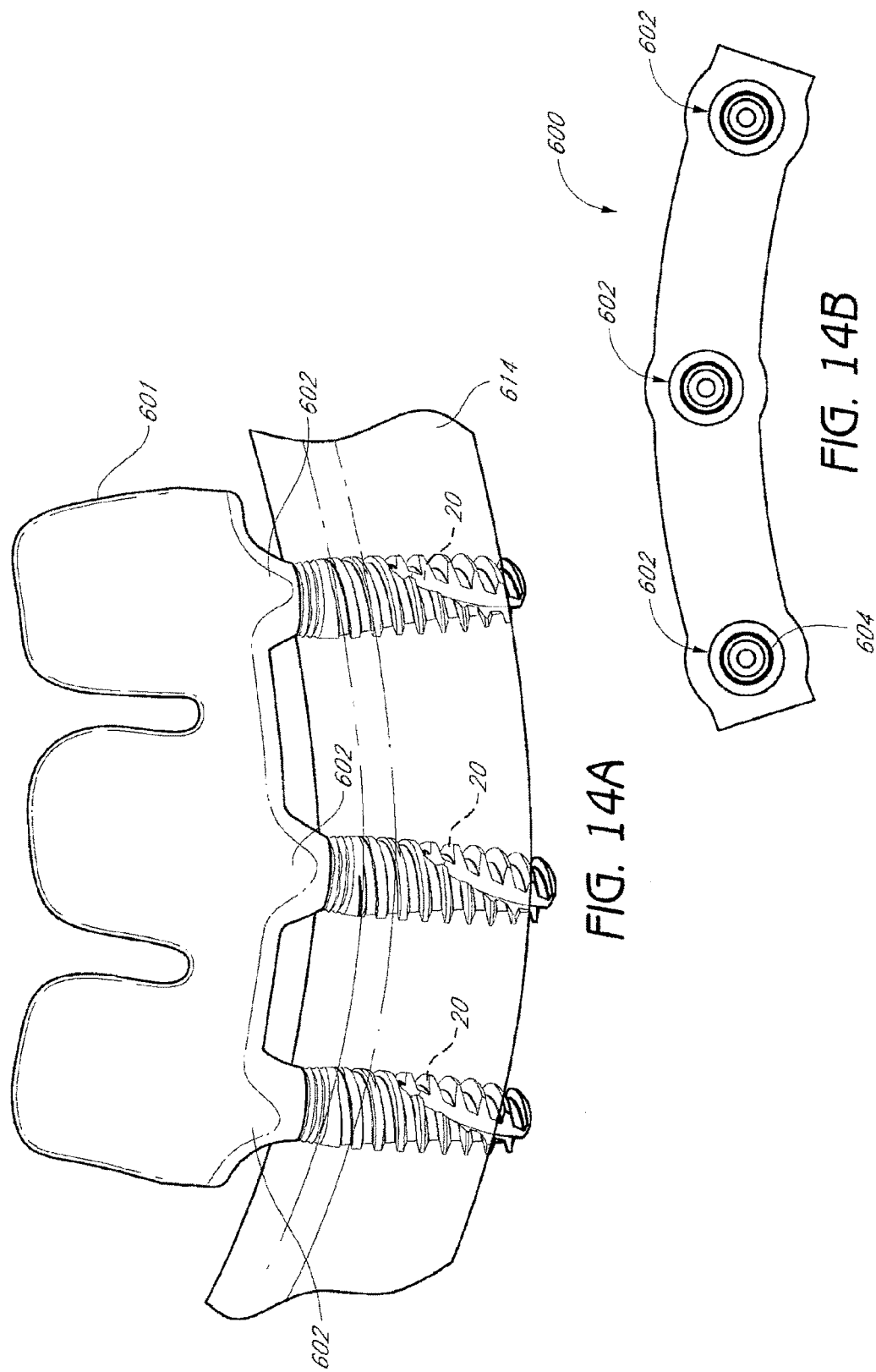
FIG. 14A is a perspective view of implant supported bridge and a set of dental implants.
FIG. 14B is a bottom view of the implant supported bridge of FIG. 14A.
Figure 14C:
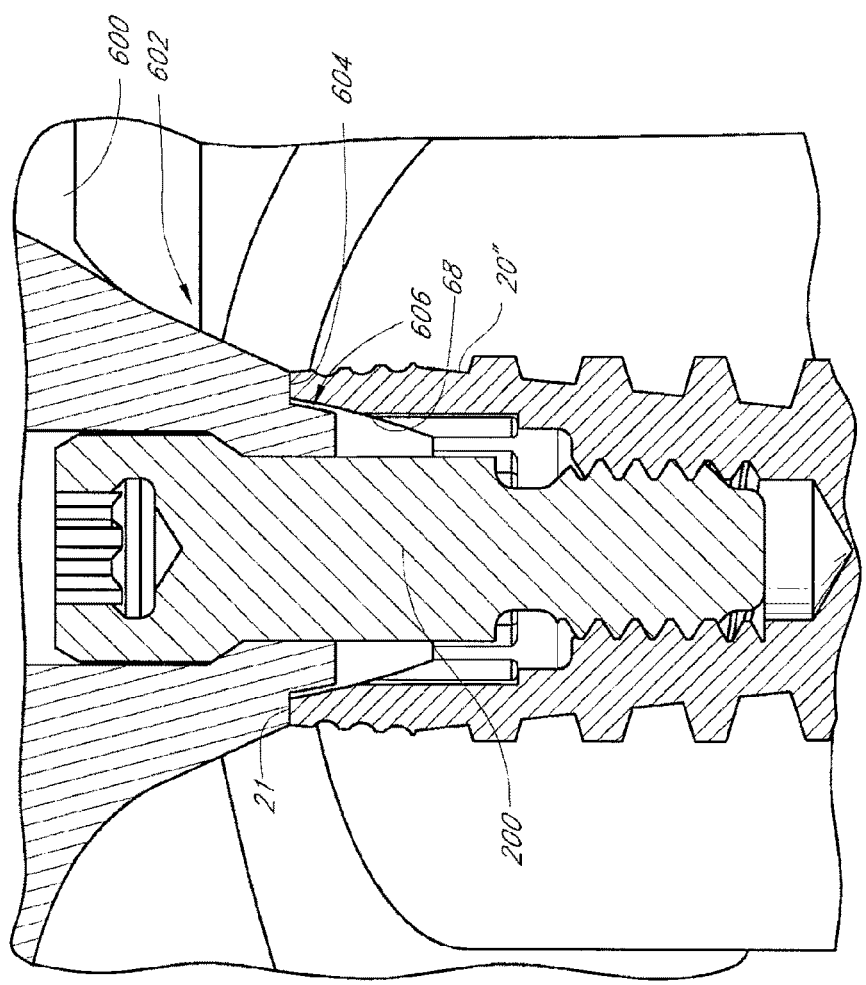
FIG. 14C is a side cross-sectional view of the implant supported bridge and one of the dental implants of FIG. 14A.

FIGS. 14A-C illustrate another embodiment of a component that can be used in combination with the implant 20. Referring to FIG. 14A, a side perspective view of an implant supported bridge 600 is shown mounted on a set of three implants 20. The bridge 600 can be used to support one or more crowns 601. It should be appreciated that in other embodiments, the bridge 600 can have a different shape and/or be configured to be supported by more or less than three implants 20. Further, the bridge 600 and crowns 601 can be specifically formed to complement the existing geometry of a patient's dental structures and to provide a natural appearance. In addition, it is anticipated that the features describe below with respect the bridge 600 can be extended to an implant supported denture. The bridge 601 can be formed of a single integral piece as shown or can be formed from a plurality of pieces attached to each other. In certain embodiments, the bridge 601 is made of titanium, ceramics (e.g., Zirconia or Alumina) or a combination of both materials.

As shown in FIGS. 14B and 14C, the bridge 600 can include a plurality of posts 602 that each correspond to one of the implants 20. Each post 602 can define a substantially flat or planar lower surface 604, which is configured to abut or rest upon the top surface 21 of the dental implant 20. Extending from the planar lower surface 604 is a centering post 606, which is generally configured to fit within the open end of the socket 66 of the implant 20 and to extend at least partially into the conical portion 68 of the implant 20. The centering post 606 can have a tapered profile as shown in FIG. 14C or can be substantially cylindrical. Preferably, the centering post 606 does not form a tapered fit with the conical portion 68 of the implant but instead is configured to form a slip fit, providing a centering function and providing lateral stability between the bridge 600 and the implant 20. This arrangement is advantageous because it can be difficult to use the tapered connection when attempting to couple a single bridge component to multiple implants. For example, as compared to a single restoration application, the precision required to align multiple posts into a tapered fit is significantly greater. This is because any misalignments between the bridge and the tapered portions 68 of the implant 20 would cause binding between the tapered surfaces of the post and the conical portions of the implant 20. However, as mentioned above, the top surface 21 of the implant 20 is sufficiently wide such that it provides adequate support for the bridge 600 to be supported on the top surfaces 21 of the implants 20 and to accommodate any misalignments. As shown in FIG. 14C, with the bottom surface 604 abutting the top surface 21 of the implant 20", a coupling screw 200 can be used to couple the bridge 600 to the implant 20".

Accordingly, an advantage of the illustrated implant 20 is that the implant 20 can be used with both an abutment 100 configured with a tapered waist 101 that emerges from the socket 66 to increase both the volume of soft tissue and the blood supply to soft tissue as described. In addition, the same implant configuration can also be used to support an implant supported bridge 601 or implant supported denture. Accordingly, one implant can serve both purposes thereby reducing the number of parts and inventory.

Figure 15B:
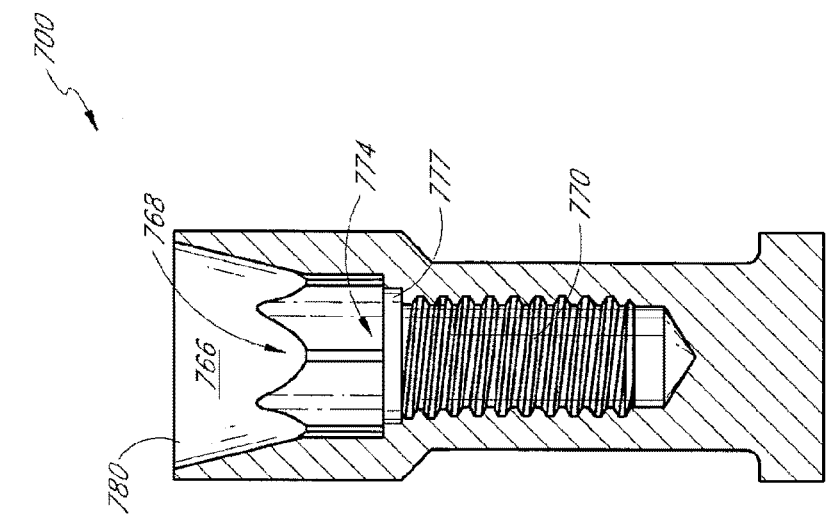
FIG. 15B is a side cross-sectional view of the implant replica of FIG. 15A.
Figure 15A:
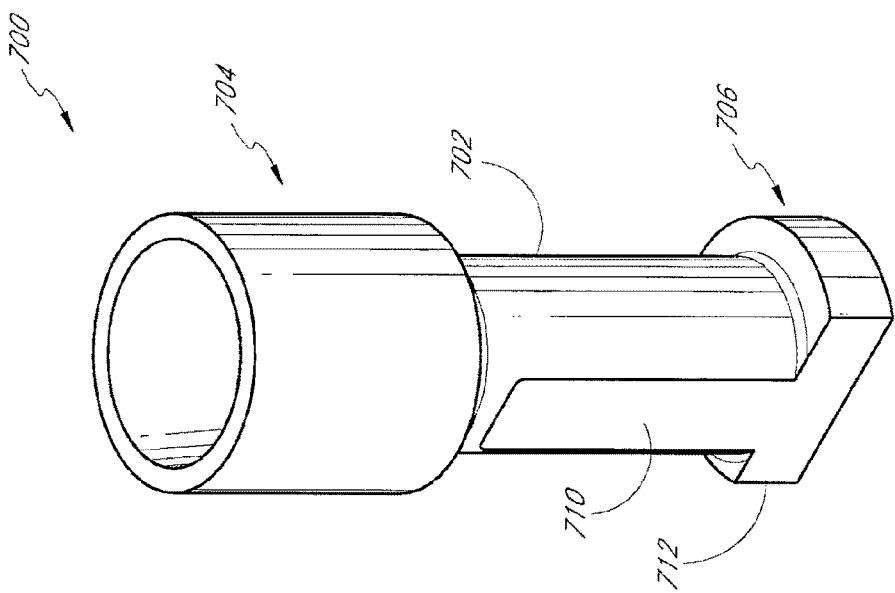
FIG. 15A is a side view of an implant replica, according to yet another embodiment.

In accordance with another embodiment, FIGS. 15A-B illustrate an embodiment of an implant replica 700. The implant replica 700 can be used in preparatory work for the creation of the implant system. As shown in FIG. 15B, the replica 700 can be configured to include all of the same internal geometry as the implant 20, illustrated above in FIGS. 1A-D. In this regard, the replica 700 is preferably used in a cast molding of a patient's alveolar bone to simulate the use and facilitate the manipulation of an implant system.

FIG. 15A illustrates that the replica 700 can include an outer surface 702 and can have an upper portion 704 and a lower portion 706. The upper portion 704 can be configured to include the features discussed above, specifically, the internal geometry as used in the implant 20. As shown in FIG. 15B, such internal geometry can include: an internal socket 766; a substantially conical or tapered portion 768 that is positioned above an interlock recess 774, which is, in turn, positioned above a threaded portion 770 of the socket 766; and a sub-chamber 777 located above the threaded chamber 770. Specific features of these elements are not listed here, but instead, can be incorporated as described above with respect to the implant 20. Thus, the replica 700 can provide the same features and geometry as the implant 20, but can be formed to be embedded into a mode or replica of the patient's mouth.

Further, as mentioned above, because the replica 700 can be used in a cast molding of a patient's alveolar bone, the outer surface 702 and the lower portion 706 of the replica 700 can be configured to facilitate the connection and/or anchoring of the replica 700 with the mold. For example, as shown in FIG. 15A, the outer surface 702 can include anti-rotational grooves or planar sections 710. Further, the lower portion 706 can be configured to include a base 712 that extends radially from the replica 700 at a different radius than other portions thereof. Thus, the replica 700 can be implanted or cast within a mold in a desired fixed orientation. Other features and modifications can be incorporated by one of skill given the present disclosure.

Figure 16A:
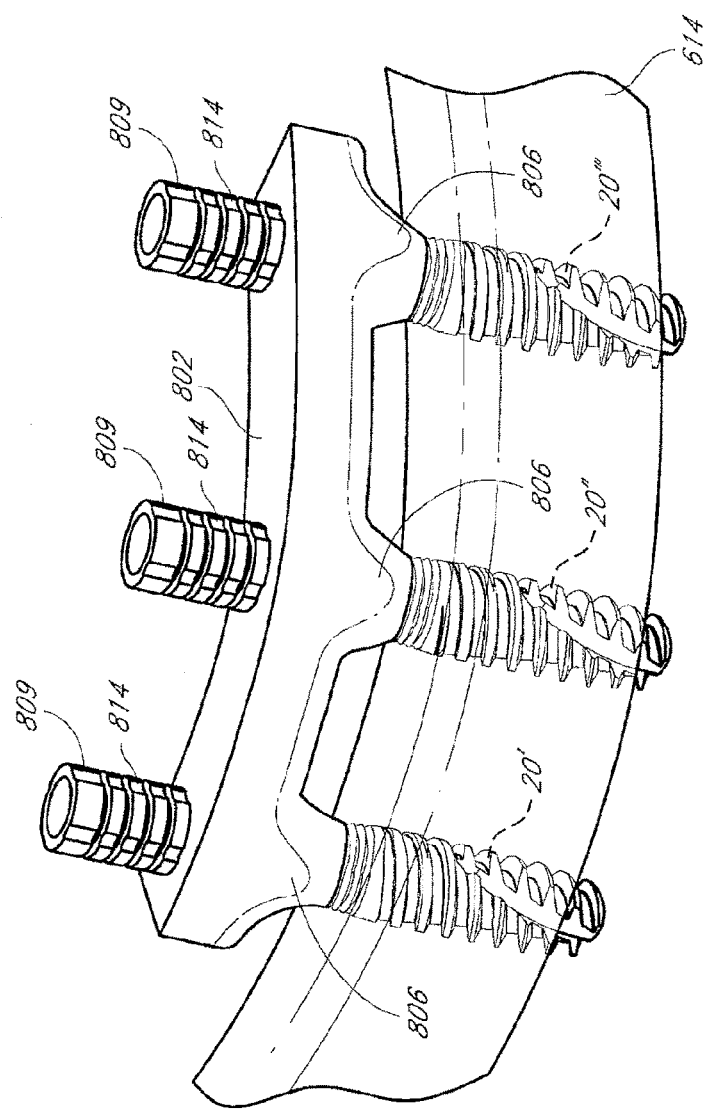
FIG. 16A is a perspective side view of a superstructure.
Figure 16B:
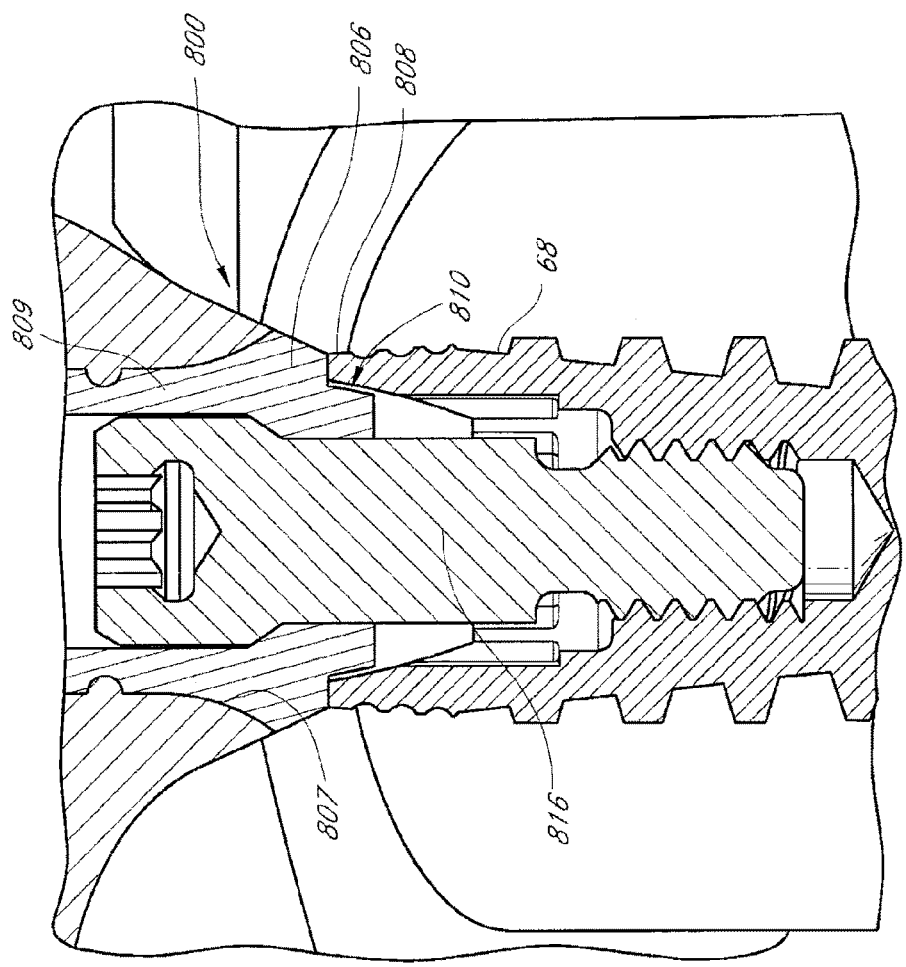
FIG. 16B is a cross-sectional side view of the superstructure of FIG. 16B.
Figure 16C:
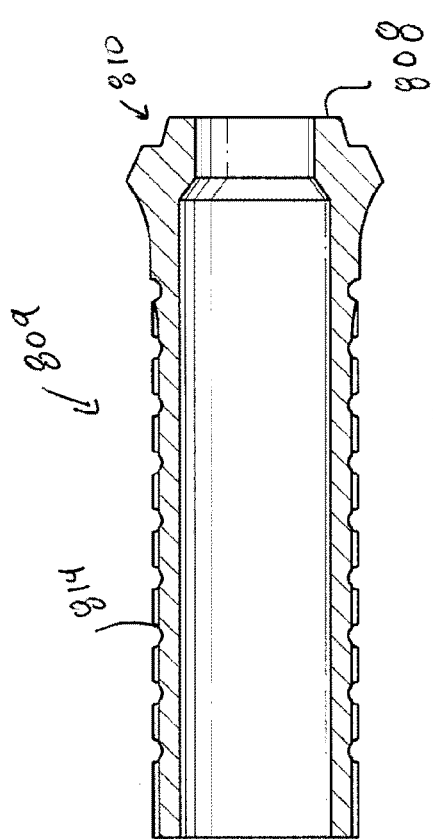
FIG. 16C is a side view of a coping of the superstructure of FIG. 16A.
Figure 16D:
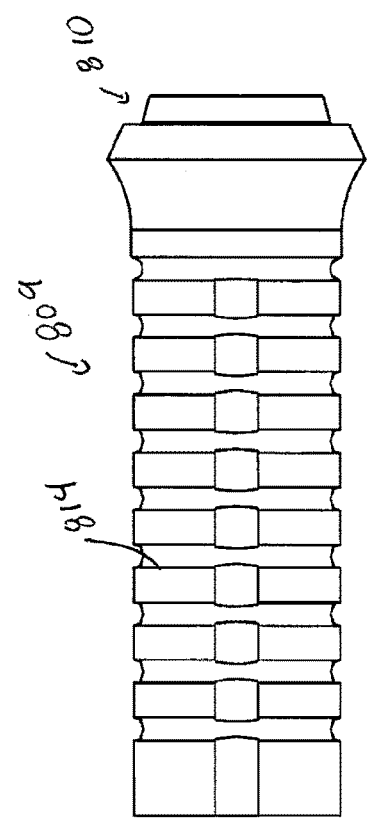
FIG. 16D is a cross-sectional view of the coping of FIG. 16A.

FIG. 16A is a side perspective view of a super structure 800, which in one embodiment can be used to create a bridge 600 or implant supported denture. As shown, the super structure can comprise first arch member 802 that comprises one or more posts 804 configured to correspond to the implants 20 positioned in a jawbone or model/reconstruction of a jawbone. As shown in FIG. 16B, each post 804 can include an opening 807 configured to receive a coping 809. The coping 809 (see also FIGS. 16C-D) can include a centering post 810 configured to fit within the socket 66 of the implants 20 and to provide a centering function without engaging the socket in a tapered fit. The coping 809, which extends through the opening 807 in the arch member 802, also includes a bottom surface 808 that is configured to abut against the top surface 21 of the implant 20. The coping 809 also includes an upper portion 814 that can extend from a top surface of the arch member 802. A coupling screw 816 can be used to attach the super structure 800 to the implant 20 and/or to a replica 700 of the implant 20.

In one embodiment, the superstructure 800 can be used in various manners to create an implant supported bridge 800 or denture. For example, the shape of the superstructure 800 can be scanned into computer and used to create the bridge. In this manner, the position and orientation of the copings can be recreated in a part that utilizes the information scanned into the computer. For example, a solid bridge can be machined from this information and/or a mold can be created. In another embodiment, the superstructure 800 can be built up and then used as part of a molding process to create a bridge. In another embodiment, the superstructure 800 can be used as part of the final bridge or an intermediate component in forming the bridge.

FIGS. 17A-C illustrate an embodiment of an abutment 900 that can be mounted onto the top surface 21 of the implant. As shown, in the illustrated arrangement, the abutment 900 can comprise a generally cylindrical body 902 having a proximal end 904 and a distal end 906. A stepped inner bore 908 can extend through the body 902 such that the abutment 900 can be coupled to the implant 20 with a coupling member (not shown). The distal end 906 of the abutment 900 can include distal facing surface 910 that is configured to abut against and cover the top surface 21 of the implant 20. Extending from the distal facing surface 910 is a tapered post 912 that is configured to be inserted into the socket 66 of the implant 20. Preferably, the post 912 has a size and shape that is configured such that the post 912 does not engage the conical portion 68 of the implant 20 in a tapered or sealed fit but instead forms a slip fit. In this manner, the abutment 900 can rest against the top surface 21 of the implant. In other embodiments, the post 912 can have a cylindrical shape.

The abutment 900 can be made of dental grade material such as gold or ceramic. In one embodiment, the embodiment the abutment 900 is made of gold and a plurality of abutments 900 can be positioned on a plurality of implants 20 or replicas 700. The abutments 900 can then be coupled together by bars that are welded or otherwise attached to the abutments to form a superstructure. The superstructure can be used as part of final bridge or denture or can be used as part of a manufacturing process for forming a final bridge or denture.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while the number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments can be made and still fall within the scope of the invention. Accordingly, it should be understood that various features and aspects of the disclosed embodiments can be combined with, or substituted for, one another in order to perform varying modes of the disclosed invention. Thus, it is intended that the scope of the present invention herein disclosed should not be limited by the particular disclosed embodiments described above, but should be determined only by a fair reading of the claims.

What is claimed is:

1. A method of installing an implant supported bridge in a patient, the method comprising:
    installing a plurality of dental implants into a patient's jawbone, each dental implant comprising:
        a body having apical end, a coronal end and a longitudinal axis, the coronal end defining a top surface that is flat and extends toward the longitudinal axis of the implant; and
        a conical open socket extending from the top surface of the dental implant towards the apical end of the dental implant, the conical open socket being positioned apically relative to the top surface; and
    directly coupling the implant supported bridge to the plurality of dental implants, the implant supported bridge comprising:
        a plurality of posts, each post comprising a flat surface and a centering post, each post corresponding to one of the plurality of dental implants with the flat surface of the post abutting the top surface of the corresponding implant and the centering post engaging the conical open socket of the corresponding implant, the centering post extending further axially in an apical direction than the flat surface when the implant supported bridge is coupled to the dental implants.

2. The method of claim 1, wherein the step of directly coupling the implant supported bridge further comprises fastening the plurality of posts to the corresponding implants with a plurality of coupling screws.

3. The method of claim 1, wherein the flat, top surface of each implant are perpendicular to the longitudinal axis of each implant.

4. The method of claim 1, wherein the implant supported bridge is adequately supported by the flat, top surfaces of the implants.

5. The method of claim 1, wherein the top surface of each dental implant has an outer periphery and an inner periphery defined by the conical open socket, wherein the distance between the outer periphery and the inner periphery is at least 0.2 millimeters.

6. The method of claim 1, further comprising positioning the implant supported bridge such that the centering posts of the plurality of posts engage the conical open sockets of the corresponding implants in a clearance fit.

7. The method of claim 6, wherein the clearance between the centering post and conical socket is configured to accommodate misalignments between the centering post and the implant.

8. The method of claim 1, further comprising positioning the implant supported bridge such that the centering posts of the plurality of posts extend partially into the conical sockets of the corresponding implants.

9. The method of claim 1, wherein each dental implant further comprises an interlock socket positioned below the conical open socket.

10. The method of claim 9, wherein the interlock socket of each implant comprises at least one flat side.

11. The method of claim 9, wherein the interlock socket is configured to engage with another dental component.

12. The method of claim 1, wherein the plurality of posts are integrally coupled.

\* \* \* \* \*